US008389475B2

(12) United States Patent
Park et al.

(10) Patent No.: US 8,389,475 B2
(45) Date of Patent: Mar. 5, 2013

(54) RELAXIN ANALOGS

(75) Inventors: Jae-Il Park, Stanford, CA (US); Sheau Yu Hsu, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 56 days.

(21) Appl. No.: 12/852,373

(22) Filed: Aug. 6, 2010

(65) Prior Publication Data

US 2011/0130332 A1 Jun. 2, 2011

Related U.S. Application Data

(60) Provisional application No. 61/273,951, filed on Aug. 10, 2009.

(51) Int. Cl.
*A61K 38/22* (2006.01)
*C07K 14/64* (2006.01)

(52) U.S. Cl. .................... 514/12.7; 424/198.1; 530/300; 530/325; 530/350

(58) Field of Classification Search ........................ None
See application file for complete search history.

(56) References Cited

U.S. PATENT DOCUMENTS

| | | | | |
|---|---|---|---|---|
| 4,758,516 | A | 7/1988 | Hudson et al. | |
| 4,871,670 | A | 10/1989 | Hudson et al. | |
| 5,811,395 | A * | 9/1998 | Schwabe et al. | 514/9.3 |

OTHER PUBLICATIONS

Bullesbach et al. Total synthesis of human relaxin and human relaxin derivatives by solid-phase peptide synthesis and site-directed chain combination. J Biol Chem 266(17): 10754-10761, 1991.*

Bullesbach et al. Functional importance of the A chain loop in relaxin and insulin. J Biol Chem 269(18): 13124-13128, 1994.*

Bullesbach et al. Structural contribution of the A-chain loop in relaxin. Int J Peptide Protein Res 46: 238-243, 1995.*

Schwabe et al. Relaxin: structures, functions, promises, and nonevolution. FASEB J 8: 1152-1160, 1994.*

Silvertown et al. Analog of H2 relaxin exhibits antagonistic properties and impairs prostate tumor growth. FASEB J 21: 754-765, 2007.*

Tang et al. Human gene 2 relaxin chain combination and folding. Biochemistry 42: 2731-2739, 2003.*

Bani; et al., "Relaxin: A Peiotropic Hormone", Gen. Pharmac. (1997), 28(1):13-22.

Hudson; et al., "Relaxin gene expression in human ovaries and the predicated structure of a human preprorelaxin by analysis of cDNA clones", The EMBO Journal (1984), 3(10):2333-2339.

Hudson; et al., "Structure of genomic clone encoding biologically active human relaxin", Nature (1983), 301:628-631.

Park; et al., "Regulation of Receptor Signaling by Relaxin A Chain Motifs", The Journal of Biological Chemistry (2008), 283(46):32099-32109.

Royce; et al., "Relaxin Reverses Airway Remodeling and Airway Dysfunction in Allergic Airways Disease", Endocrinology (2009), 150(6):2692-2699.

Samuel; et al., "Relaxin in cardiovascular and renal disease", Kidney International (2006), 69:1498-1502.

Samuel; et al., "The Effects of Relaxin on Extracellular Matrix Remodeling in Health and Fibrotic Disease", Adv. Exp. Med. Biol. (2007), 612:88-103.

Van Der Westhuizen; et al., "Relaxin family peptide receptors—from orphans to therapeutic targets", Drug Discovery Today (2008), 13(15/16):640-651.

* cited by examiner

*Primary Examiner* — Bridget E Bunner
(74) *Attorney, Agent, or Firm* — Bozicevic, Field & Francis LLP; Pamela J. Sherwood

(57) ABSTRACT

Human relaxin analogs, polypeptide compositions related thereto, as well as nucleotide compositions encoding the same, are provided.

20 Claims, 9 Drawing Sheets

RELAXIN ANALOGS

GOVERNMENT RIGHTS

The invention was made with government support under National Institutes of Health Grant HD47606. The Government has certain rights in the invention.

The present invention relates to relaxin analogs, and uses thereof. The present invention further relates to compositions and formulations comprising relaxin analogs and their uses. The present invention also relates to compositions and formulations comprising the relaxin analogs, its derivatives and/or relaxin or other agent wherein such composition exhibits an additive or synergistic effect.

BACKGROUND OF THE INVENTION

Relaxin is a pregnancy hormone discovered in 1926 (Hisaw (1926) *Proc. Soc. Exp. Biol. Med.* 23: 661-663), based on its ability to relax the public ligament in guinea pig. Mature human relaxin is a hormonal peptide of approximately 6000 daltons known to be responsible for remodelling the reproductive tract before parturition, thus facilitating the birth process. A concise review of relaxin was provided by Sherwood, D. in The Physiology of Reproduction, Chapter 16, "Relaxin", Knobil, E. and Neill, J., et al. (eds.), (Raven Press Ltd., New York), pp. 585-673 (1988). Relaxin has local autocrine and/or paracrine roles that contribute to connective tissue remodeling at the maternal-fetal interface during late pregnancy and at parturition, including an increase in the expression of the genes, proteins, and enzyme activities of the matrix metalloproteinases interstitial collagenase (MMP-1), stromelysin (MMP-3), and gelatinase B (MMP-9).

In humans, the relaxin gene family contains a total of seven members: relaxin H1 (RLN1), relaxin H2 (RLN2), relaxin 3/INSL7 (RLN3), INSL3/RLF, INSL4/EPIL, INSL5/RIF2, and INSL6/RIF1 (Hudson et al. (1983) *Nature* 301:628-631; Hudson et al. (1984) *EMBO Journal* 3:2333-2339; U.S. Pat. Nos. 4,758,516 and 4,871,670). The primary translation product of H2 relaxin is a preprorelaxin consisting of a 24 amino acid signal sequence followed by a B chain of about 29 amino acids, a connecting peptide of 104-107 amino acids, and an A chain of about 24 amino acids. Among these family members, RLN2 and INSL3 signal through two leucine-rich repeat-containing GPCRs, LGR7 (RFXR1) and/or LGR8 (RFXR2). Whereas RLN2 is capable of activating both LGR7 and LGR8, INSL3 is a selective ligand for LGR8. In addition to the better characterized RLN2 and INSL3, RLN3 was shown to activate LGR7, GPCR135, and GPCR142, but not LGR8 (6-10); therefore, the relaxin family peptides exhibit overlapping specificity on the activation of LGR7 and LGR8.

Evidence has accumulated to suggest that relaxin is more than a hormone of pregnancy and acts on cells and tissues other than those of the female reproductive system. Relaxin causes a widening of blood vessels (vasodilatation) in the kidney, mesocaecum, lung and peripheral vasculature, which leads to increased blood flow or perfusion rates in these tissues (Bani et al (1997) Gen. Pharmacol. 28, 13-22). It also stimulates an increase in heart rate and coronary blood flow, and increases both glomerular filtration rate and renal plasma flow (Bani et al (1997) Gen. Pharmacol. 28, 13-22). The brain is another target tissue for relaxin where the peptide has been shown to bind to receptors. In addition to the role in remodeling of reproductive tissues, relaxin has been shown to effect endometrial differentiation during embryo implantation, nipple and mammary gland development, angiogenesis, wound healing, and renal cardiovascular responses. Furthermore, recent studies have shown that relaxin prolongs the survival of tumor-bearing mice by enhancing the degradation of the extracellular matrix, thereby slowing down tumor growth.

In contrast, INSL3 is essential for testis descent in rodents and contributes to the regulation of, 1) male germ cell apoptosis; 2) initiation of meiotic progression of arrested oocytes in preovulatory follicles; and 3) the positioning of the female gonad during development. Although the importance of LGR7 and LGR8 in human RLN1 and RLN2 signaling remains to be studied, in vitro evidence indicated that human RLN2 could effect LGR8 signaling in vivo. Based on its pleiotropic effects on tissue remodeling, relaxin has been the subject for clinical trials aimed to treat scleroderma, pre-eclampsia, congestive heart failure, and to enhance cervical ripening during the third trimester of pregnancy. The finding that human RLN2 is capable of activating both LGR7 and LGR8 raises the possibility that clinical applications of human RLN2 could pose unwanted responses in the LGR8 signaling pathway in patients, which could include effects on spermatogenesis and ovarian follicle development.

Therefore, a better understanding of the molecular mechanisms underlying the interaction of human RLN2 and its receptors, as well as the generation of an LGR7-specific human relaxin analog are of great interest.

SUMMARY OF THE INVENTION

Relaxin analogs, polypeptide compositions related thereto, as well as nucleotide compositions encoding the same, are provided. The analog polypeptides of the invention comprise at least one amino acid substitution relative to the wild-type protein, and have altered receptor selectivity or activity relative to the wild-type protein. The peptides may be provided as pharmaceutically acceptable compositions for human or animal administration, by various therapeutic routes. Peptides may be isolated in purified or homogenous form free of contaminating peptides and proteins, or in a form of about 90-99% purity.

The relaxin analogs of the invention have altered receptor specificity as compared to the reference, naturally occurring forms, e.g. wild-type human RLN2. In some embodiments, a Type I analog is provided, which has a reduced affinity for the receptor LGR8 (RFXR2); and/or an increased affinity for the receptor LGR7 (RFXR1). In other embodiments, a Type II analog is provided, which exhibits an enhanced bioactivity upon both receptors. Polypeptides of interest include processed forms of the relaxin analogs of the invention, which comprise an A chain and a B chain, which A chain and B chain may be linked through a disulfide bond; and unprocessed forms in which the A chain and B chain are linked through the C chain or through a truncated C chain. In other embodiments, an A chain analog is provided.

The analogs are useful as therapeutic agents. Conditions treatable with relaxin analogs include, without limitation, conditions that benefit from collagen or extracellular matrix remodelling. Included are induction of labor, treatment of pre-eclampsia, congestive heart failure, treatment of endometriosis, treatment of skin conditions such as scleroderma, treatment of fibrosis, treatment of hypertension. Relaxin has been implicated in the dilation of blood vessels' smooth muscle cells, for treatment of hypertension. Relaxin is also been useful in the treatment of severe chronic pain, particularly pain arising from stretching, swelling, or dislocation of tissues.

Human wild-type RLN2 is capable of activating both LGR7 and LGR8, and therefore clinical applications of human RLN2 may pose unwanted responses in the LGR8 signaling pathway in patients, which could include effects on spermatogenesis and ovarian follicle development. The type I relaxin analogs of the invention allow relaxin treatment to specifically target the LGR7 receptor, which is the prime target for most clinical applications of relaxins. Type II analogs, which have increased overall potencies on the two relaxin receptors relative to the wild-type polypeptide, find use clinically where receptor selectivity is not required.

DESCRIPTION OF THE SPECIFIC EMBODIMENTS

Figure 1:
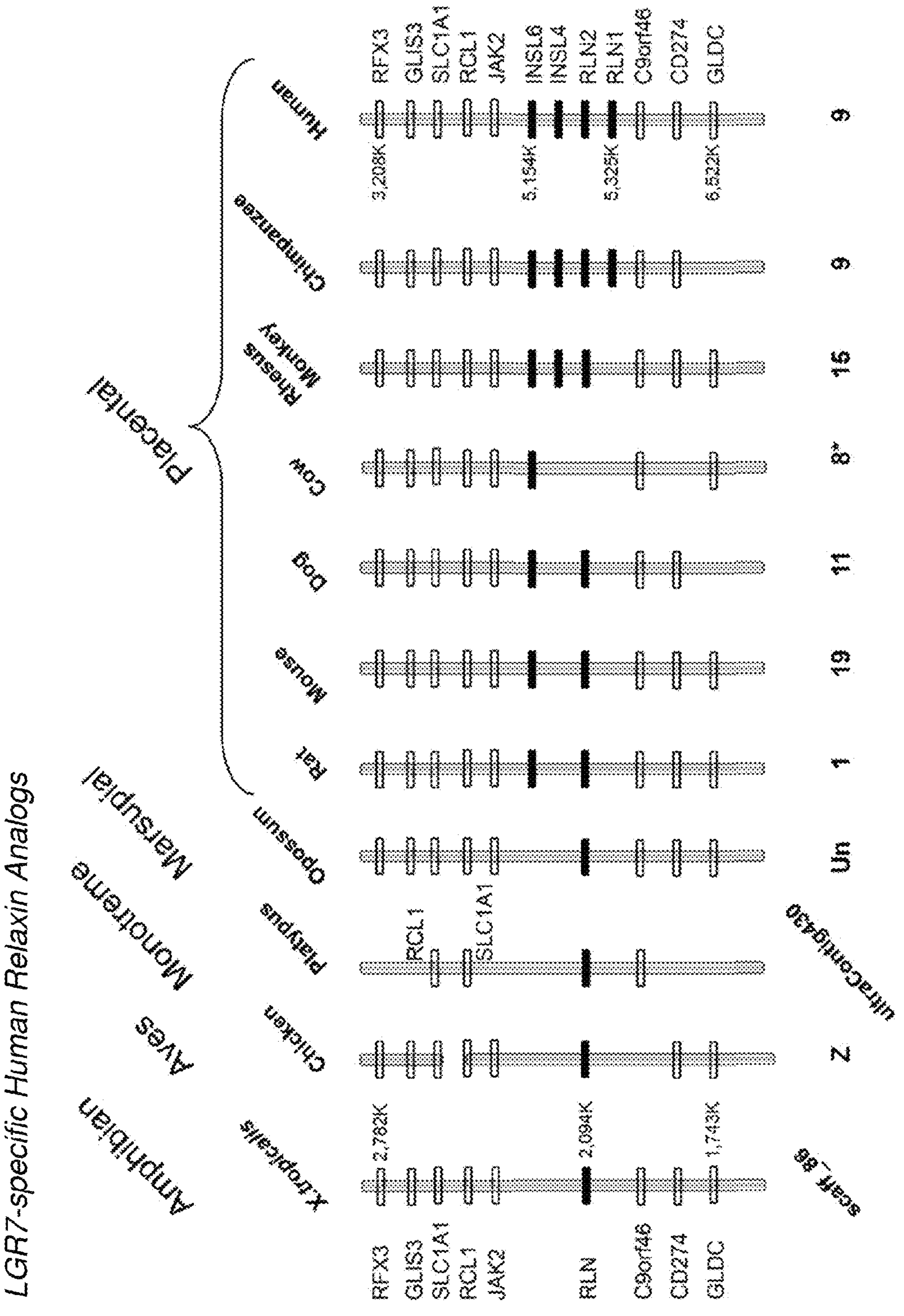
FIG. 1. Syntenic mapping of the RLN1/RLN2/INSL4/INSL6 locus in tetrapods. Schematic representation of relaxin locus syntenic to the RLN1/RLN2/INSL4/INSL6 locus on human chromosome 9 in chimpanzee (*P. troglodytes*), Rhesus monkey (*M. mulatta*), cow (*B. taurus*), dog (*C. familiaris*), mouse (*M. musculus*), rat (*R. norvegicus*), the gray short-tailed opossum (*M. domestica*), platypus (*O. anatinus*), chicken (*G. gallus*), and the clawed frog (*X. tropicalis*). The relaxin family genes on the syntenic relaxin family locus B (RFLB) locus of different vertebrates are indicated by black rectangles, whereas, neighboring genes are indicated by blank rectangles. The chromosomal numbers or the genomic contig numbers are indicated at the bottom of the schematic representation of each genomic fragment. The positions of select genes in the genomes of human and *X. tropicalis* are also indicated (*), part of the syntenic region on chromosome 8 of cow is mapped to unknown chromosome in the GenBank™.

Relaxin analogs, polypeptide compositions related thereto, as well as nucleotide compositions encoding the same, are provided. The subject polypeptide and/or nucleic acid compositions find use in a variety of different applications, including in vivo prophylactic and therapeutic purposes; as immunogens for producing antibodies; in screening for biologically active agents; and the like.

It is shown herein that an amino acid substitution at one or more of SEQ ID NO:3 residue 16, and SEQ ID NO:3 residue 17, where the naturally occurring amino acids threonine and lysine are replaced with a small neutral amino acid results in enhanced LGR8-activation activity. In some embodiments of the invention, a relaxin analog comprises an amino acid substitution at one or both of SEQ ID NO:3 residue 16, and SEQ ID NO:3 residue 17, wherein the analog has increased bioactivity relative to the wild-type polypeptide.

It is also shown herein that that an amino acid substitution at SEQ ID NO:3 residue 23, where the naturally occurring amino acid phenylalanine is replaced with a small neutral amino acid ablates LGR8, but not LGR7, activation activity. In some embodiments of the invention, a relaxin analog comprises an amino acid substitution at SEQ ID NO:3 residue 23, wherein the analog has a reduced affinity for the receptor LGR8 relative to the wild-type polypeptide.

Relaxin is a hormone with a number of important functions, which include the modulation of the reproductive physiology of human beings and other mammals, including, but not limited to, maintaining pregnancy, effecting parturition, and enhancing sperm motility as an aid in fertilization. Relaxin has significant effects on connective tissue. Relaxin has been implicated in the dilation of cardiac and blood vessels' smooth muscle cells, and has also been used in the treatment of severe chronic pain, particularly pain arising from stretching, swelling, or dislocation of tissues. Relaxin has also been shown to decrease collagen formation and secretion, increase collagenase production, influence renal vasodilation, increase vascular endothelial growth factor expression and angiogenesis, promote dilation of blood vessels, and inhibit release of histamine.

In one aspect of the invention there is provided a method for the treatment of one or more of: vascular disease including coronary artery disease, congestive heart failure, peripheral vascular disease; treatment of arterial hypertension; diseases related to uncontrolled or abnormal collagen or fibronectin formation, including without limitation fibrotic disorders (including fibrosis of lung, heart and cardiovascular system, kidney and genitourinary tract, gastrointestinal system, cutaneous, rheumatologic and hepatobiliary systems); scleroderma; kidney disease associated with vascular disease, interstitial fibrosis, glomerulosclerosis, or other kidney disorders; endometrial disorders including infertility due to impaired implantation; delayed onset of labour, impaired cervical ripening, and prevention of prolonged labour due to fetal dystocia; placental insufficiency; which comprises administering to a subject in need of any such treatments a therapeutically effective amount of human relaxin analog thereof as herein defined, optionally in association with one or more pharmaceutically acceptable carriers and/diluents and/or excipients.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Relaxin as used herein generally refers to human relaxin RLN2 unless a species or variant is otherwise specified, including full length relaxin or a portion of the relaxin molecule that retains biological activity. Relaxin is a peptide hormone produced by the corpora lutea of ovaries during pregnancy in many mammalian species, including man. The secretion of the hormone into the blood stream just before parturition results in a marked softening and lengthening of the pubic symphysis and a softening of the cervix, which facilitates the birth process. By inhibiting uterine contractions, relaxin may influence the timing of parturition. Like insulin, relaxin consists of two peptide chains, A and B, covalently linked by disulfide bonds. By further analogy to insulin, the two peptides are synthesized as a single-chain precursor polypeptide with the B chain at the NH2-terminus.

In the human there are three non-allelic relaxin genes, RLN1, RLN2 and RLN3. RLN1 and RLN2 share high sequence homology. The RLN2 has two alternatively spliced variant transcripts, isoform 1 is described in Genbank accession number NM_134441; and isoform 2, which includes an alternate exon, that causes a frameshift and use of an early stop codon, is described at Genbank accession number NP_005050.2. For the purposes of the present invention, the polypeptide encoded by the isoform 1 is of interest.

The activities of relaxin, which are also mediated by the analogs provided herein, are reviewed by Samuel and Hewitson (2006) Kidney International 69, 1498-1502; Goyce et al. (2009) Endocrinology 150: 2692-2699; Westhuizen et al. (2008) Drug Discovery Today 13:640; and Samuel et al. (2007), chapter 7 in in Relaxin and Related Peptides; ed. Agoulnik, Landes Bioscience; each herein specifically incorporated by reference.

The unprocessed human RLN2 polypeptide has the amino acid sequence (SEQ ID NO:1), where the residues comprising the mature polypeptides are underlined:

```
MPRLFFFHLLGVCLLLNQFSRAVADSWMEEVIKLCGRELVRAQIAICGM
STWSKRSLSQEDAPQTPRPVAEIVPSFINKDTETINMMSEFVANLPQEL
KLTLSEMQPALPQLQQHVPVLKDSSLLFEEFKKLIRNRQSEAADSSPSE
LKYLGLDTHSRKKRQLYSALANKCCHVGCTKRSLARFC
```

The sequence of the wild-type human mature B chain (SEQ ID NO:2) is: SWMEEVIKLCGRELVRAQIAICGMSTWS (SEQ ID NO:2). In addition to the wild-type, or naturally occurring B chain, biologically active analogs are known in the art and may be combined with the A chain analogs of the present invention, for example as described by Silvertown et al. (2007) FASEB J. 21, 754-765; U.S. Pat. No. 5,811,395, entitled "Relaxin analogs and derivatives methods and uses thereof"; U.S. Pat. No. 6,200,953, entitled "Relaxin analogs and derivatives compositions"; Hossain et al. (2009) Chem Biol Drug Des. 2009 January; 73(1):46-52; and Bullesbach et al. (1992) *J. Biol. Chem.* 267, 22957-22960; each herein specifically incorporated by reference.

The sequence of the wild-type human RLN2 A chain is QLYSALANKCCHVGCTKRSLARFC (SEQ ID NO:3), which sequence is the reference for describing analog sequences.

Relaxin Receptor. Human RLN2 activates two receptors, LGR7 (RFXR1) and LGR8 (RFXR2). As described by Hsu et al. (2002) Science 295: 671-674, RLN2 activates both of these receptors, resulting in dose-dependent increase in cAMP production. For reference purposes, the genetic sequences of these proteins are known and publicly available, for example at Genbank accession number NP_570718 (LGR8); and Genbank accession number NM_021634 (LGR7). The selectivity and activity of RLN2 and RLN2 analogs may be determined by various assays, including those described in the Examples herein. For example, dose dependent cyclic AMP production in cells expressing one or both of the receptors may be determined; specific binding to the receptor; and assays directed at known biological effects of relaxin, such as the effects on connective tissues; parturition; and the like.

Figure 2:
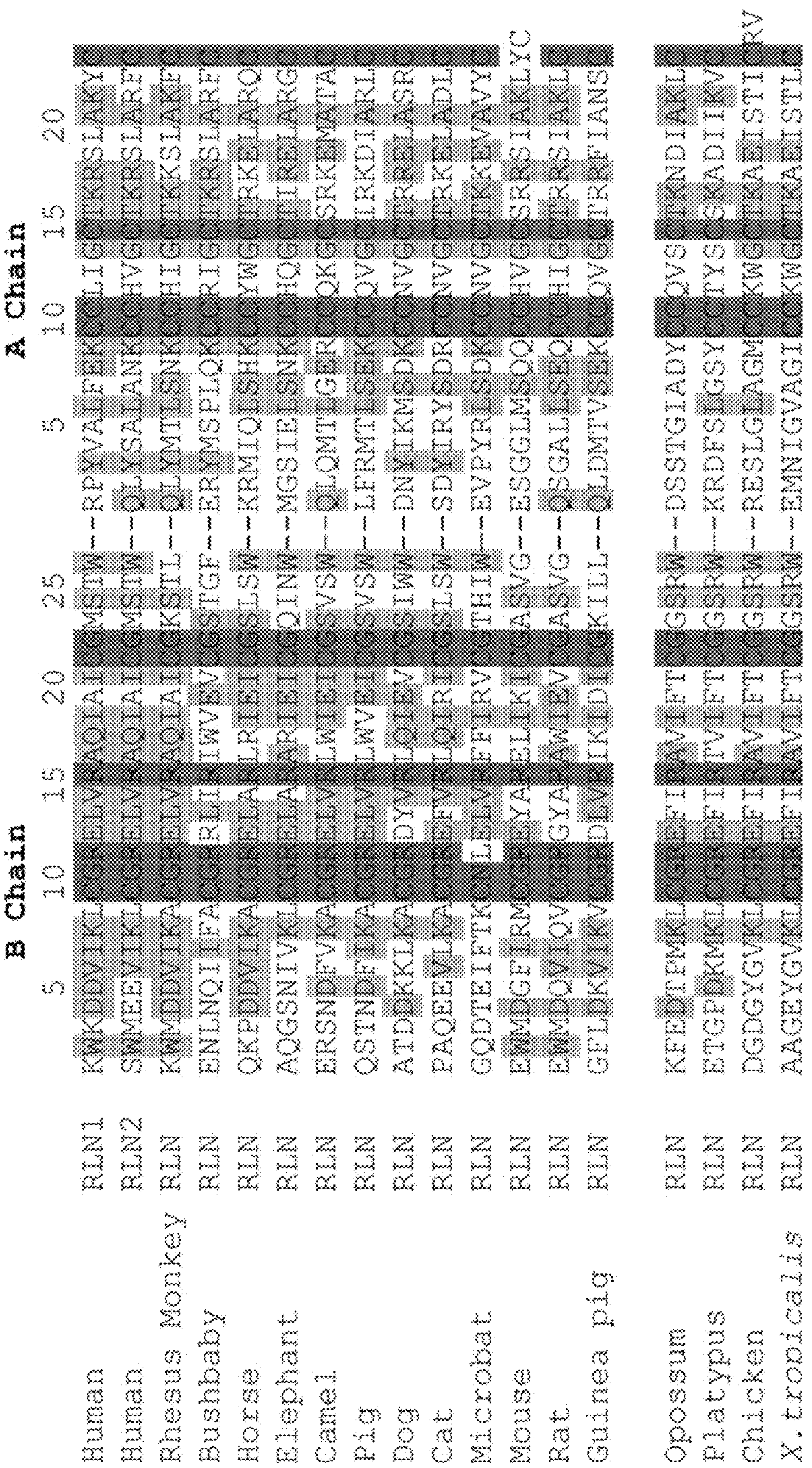
FIG. 2. Alignment of amino acid sequences of the B and A chains of relaxin peptides from the RFLB of 17 representative tetrapods as set forth in SEQ ID NO:7-24. Residues that are completely conserved in all species analyzed are highlighted by a dark background. Resides that are conserved in at least five sequences are indicated by a gray background. Positions of residues are indicated by numbers on top of the alignment.

Relaxin A Chain Analog. As used herein, A chain analogs provide for one or more amino acid changes relative to SEQ ID NO:3; and provide for altered biological activity. The altered activity may be increased selectivity for activation of the receptor LGR7; decreased selectivity for the activation of LGR8; or increased overall receptor activation. It will be understood by one of skill in the art that amino acid substitutions set forth with respect to the human RLN2 A chain may also be made in the A chain of RLN2 from other animals, particularly other mammals, and particularly placental mammals, for example as shown in the alignment of FIG. 2. The amino acid substitutions may also be combined with other amino acid substitutions that enhance, or that do not adversely affect the biological activity, for example as described by Bullesbach and Schwabe (1987) *J. Biol. Chem.* 262, 12496-12501; Bullesbach and Schwabe (2006) *J. Biol. Chem.* 281, 26136-26143; and Rosengren et al. (2006) *J. Biol. Chem.* 281, 28287-28295, each herein specifically incorporated by reference.

A type I analog of the invention comprises an amino acid substitution at residue 23 of a relaxin A chain, particularly a relaxin 2 A chain, for example as set forth in Table 2. The naturally occurring amino acid may be replaced with a small amino acid, or a conservative variation thereof. Specific substitutions of interest include Ile, Leu, Ser, Gly, Ala, and Thr. A substitution at residue 22 may also be made and combined with the residue 23 substitution. In some embodiments the relaxin analog comprises the sequence:

```
QLYSALANKCCHVGCTKRSLARXC     (SEQ ID NO: 5)
```

where X is an amino acid other than phenylalanine. In some embodiments X is selected from ala, leu, gly, ser, ile, and thr.

A type II analog of the invention comprises an amino acid substitution at one or both of residue 16, and residue 17 of a relaxin A chain, particularly a relaxin 2 A chain, for example as set forth in Table 2. The naturally occurring amino acid may be replaced with a small amino acid, or a conservative variation thereof. Specific substitutions of interest include Ile, Leu, Ser, Gly and Ala. In some embodiments the relaxin analog comprises the sequence:

QLYSALANKCCHVGC$X_1X_2$RSLARFC     (SEQ ID NO: 6)

wherein $X_1$ and $X_2$ are independently selected from amino acids other than threonine and lysine. In some embodiments one or both of $X_1$ and $X_2$ are Ile, Leu, Gly or Ala.

Relaxin C chain. The wild-type, or naturally occurring RLN2 comprises a C chain, which is cleaved during maturation and is not present in the mature biologically active polypeptide. The wild-type C chain of human RLN2 has the sequence: (SEQ ID NO:4) KRSLSQEDAPQTPRPVAEIVPSFINKDTETINMMSEFVANLPQELKLTLSEMQPALPQLQQHVPV LKDSSLLFEEFKKLIRNRQSEAADSSPSELKYLGLDTHSRKKR. This sequence is fused to the B and A chains, for example as shown in SEQ ID NO:1. In some embodiments of the invention, the C chain of RLN2 is replaced with truncated C domain sequence, where the truncated domain consists of 2, 3, 4, 5, 6, 7, 8, 9, 10 or more amino acids of the C domain, generally the truncated domain retains the sequence at the carboxy terminus, e.g. SEQ ID NO:4, residues 1-5; residues 1-6, residues 1-7, residues 1-8; and the like. Usually the truncated C chain will comprise the cleavage motif, "RXXR" or "KR". The truncated C domain may be combined wild-type A and B chain sequences, or with analog sequences as described herein.

Polypeptides

Relaxin analogs are provided. The peptides may be provided as pharmaceutically acceptable compositions for human or animal administration, by various therapeutic routes. Peptides are usually isolated in purified or homogenous form free of contaminating peptides and proteins, or in a form of about 90-99% purity.

The relaxin analogs of the invention have altered receptor specificity as compared to the reference, naturally occurring forms. In some embodiments, a Type I analog is provided, which has a reduced affinity for the receptor LGR8 (RFXR2); and/or an increased affinity for the receptor LGR7 (RFXR1). In other embodiments, a Type II analog is provided, which exhibits an enhanced bioactivity upon both receptors. Polypeptides of interest include processed forms of the relaxin analogs of the invention, which comprise an A chain and a B chain, which A chain and B chain may be linked through a disulfide bond; and unprocessed forms in which the A chain and B chain are linked through the C chain or through a truncated C chain. In other embodiments, an A chain analog is provided. The A chain analogs of the invention may be combined with a wild-type B chain, or with an analog thereof.

The sequence of the polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids.

The polypeptides of the invention biologically active molecule may be conjugated to a pharmaceutically acceptable polymer to increase its serum half-life. The polymer may or may not have its own biological activity. The suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof.

Polypeptides may be PEGylated, by which is meant the covalent attachment of at least one molecule of polyethylene glycol. The average molecular weight of the reactant PEG is preferably between about 5,000 and about 50,000 daltons, more preferably between about 10,000 and about 40,000 daltons, and most preferably between about 15,000 and about 30,000 daltons. Particularly preferred are PEGs having nominal average sizes of about 20,000 and about 25,000 daltons. The method of attachment is not critical, but preferably does not alter, or only minimally alters, the activity of the polypeptide. Preferably the increase in half-life is greater than any decrease in biological activity. A preferred method of attachment is via N-terminal linkage to a polypeptide.

By "increase in serum half-life" is meant the positive change in circulating half-life of a modified biologically active molecule relative to its non-modified form. Serum half-life is measured by taking blood samples at various time points after administration of the biologically active molecule, and determining the concentration of that molecule in each sample. Correlation of the serum concentration with time allows calculation of the serum half-life. The increase is desirably at least about two-fold, but a smaller increase may be useful, for example where it enables a satisfactory dosing regimen or avoids a toxic effect. Preferably the increase is at least about three-fold, more preferably at least about five-fold, and most preferably at least about ten-fold, and most preferably at least about fifteen-fold.

The polypeptide can be produced by any suitable means, such as expression in a recombinant host cell or by chemical synthesis. Various commercial synthetic apparatuses are available, for example automated synthesizers by Applied Biosystems Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

The polypeptide can be linked to a polymer through any available functionality using standard methods well known in the art. It is preferred that the biologically active molecule be linked at only one position in order to minimize any disruption of its activity and to produce a pharmacologically uniform product. Nonlimiting examples of functional groups on either the polymer or biologically active molecule which can be used to form such linkages include amine and carboxy groups, thiol groups such as in cysteine resides, aldehydes and ketones, and hydroxy groups as can be found in serine, threonine, tyrosine, hydroxyproline and hydroxylysine residues.

The polymer can be activated by coupling a reactive group such as trichloro-s-triazine (Abuchowski et al., (1977), *J. Biol. Chem.* 252:3582-3586), carbonylimidazole (Beauchamp et al., (1983), *Anal. Biochem.* 131:25-33), or succinimidyl succinate (Abuchowski et al., (1984), *Cancer Biochem. Biophys.* 7:175-186) in order to react with an amine functionality on the biologically active molecule. Another coupling method involves formation of a glyoxylyl group on one molecule and an aminooxy, hydrazide. or semicarbazide group on the other molecule to be conjugated (Fields and Dixon, (1968), *Biochem. J.* 108:883-887; Gaertner et al., (1992), *Bioconjugate Chem.* 3:262-268; Geoghegan and Stroh, (1992), *Bioconjugate Chem.* 3:138-146; Gaertner et al., (1994), *J. Biol. Chem.* 269:7224-7230). Other methods involve formation of an active ester at a free alcohol group of the first molecule to be conjugated using chloroformate or disuccinimidylcarbonate, which can then be conjugated to an amine group on the other molecule to be coupled (Veronese et al., (1985), *Biochem. and Biotech.* 11:141-152; Nitecki et al., U.S. Pat. No. 5,089,261; Nitecki, U.S. Pat. No. 5,281,698). Other reactive groups which may be attached via free alcohol groups are set forth in Wright, published European patent application 0 539 167 A2, which also describes the use of imidates for coupling via free amine groups.

Pharmaceutical compositions comprising a conjugate of a biologically active molecule and a polymer can be prepared by mixing the conjugate with any pharmaceutically acceptable component, such as, for example, a carrier, a medicinal agent, an adjuvant, a diluent, and the like, as well as combinations of any two or more thereof. Suitable pharmaceutical carriers, medicinal agents, adjuvants, and diluents are described in "Remington's Pharmaceutical Sciences," $18^{th}$ edition, by E. W. Martin (Mack Publ. Co., Easton, Pa.).

Uses

As analogs for relaxin, the polypeptides of the invention have important roles in the physiology of pregnancy, reproductive development, biological processes relating to smooth muscle and to connective tissue; and the like. Uses include, without limitation, induction of labor; treatment of scleroderma; reduction of hypertension, treatment of congestive heart failure, and treatment of other disorders associated with collagen and fibrinogen metabolism, including fibrosis Formulations of polypeptides of the invention find clinical use.

Polypeptides of the invention affect epithelial cells, blood vessels, stromal cells (putative fibroblasts), and smooth muscle in the cervix and vagina, e.g. by promoting the onset of labor, increasing endometrial cells, inducing synthesis of mucins, regulating pituitary prolactin, oxytocin, and vasopressin release, etc.

These molecules also have important effects on the vascular system. Polypeptides of the invention are angiogenic in the endometrial lining, and plays a role in the attachment of the embryo to the uterus. They can be administered to increase blood flow and vasodilation of vascular beds. Methods for the use of relaxin to increase angiogenesis are described in U.S. Pat. No. 6,211,147. Relaxin and other agonists can act as a factor in protection against arteriosclerosis and ischemic or thrombotic pathologies, by inducing dilation of blood vessels' smooth muscle cells which results in an increment of blood flow; inhibits coagulation processes, intensifies the fibrinolysis and lowers blood concentration of lipids and sodium. This effect is mediated both directly, and through release NO and ANP, which largely contribute to the effect on vessel walls and blood components. See, for example, U.S. Pat. No. 5,952,296.

Polypeptides of the invention also act as an anti-fibrinolytic agent by decreasing collagen production, increasing collagen breakdown, and reducing the production of the collagenase inhibitor, TIMP Agonists may act directly on stromal cells to promote remodeling of the extracellular matrix. Remodeling of connective tissue has potential for clinical applications, for example in the treatment of systemic sclerosis, or scleroderma, and as a cervical softening agent at term.

Polypeptides of the invention also find use in the treatment of fibromyalgia, and may also include the treatment of neurological disorders, for example Alzheimer's disease, Parkinson's, and/or other conditions such as ADD.

Another use of the polypeptides of the invention is as an analgesic and palliative for intractable pain (see U.S. Pat. No. 5,656,592). Although relaxin and other agonists can be used generally as an analgesic and palliative for pain, the conditions most amenable to its therapeutic administration are those in which unusual stress is chronically placed on tissues because of an acquired or inherent malformation which results in the displacement of tissues from their natural disposition in the body. These agents find utility, for example, in the treatment of severe chronic pain, particularly pain arising from stretching, swelling, or dislocation of tissues.

Formulations

The compounds of this invention can be incorporated into a variety of formulations for therapeutic administration.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1).

Dosage amount and interval may be adjusted individually to provide serum levels of the active moiety which are sufficient to maintain the relaxin activity and effects.

While human dosage levels for treating many of the above-identified relaxin related diseases or disorders have yet to be optimized, a daily dose is from about 0.05 to 500.0 μg/kg of body weight per day, preferably about 5.0 to 200.0 μg/kg, and most preferably about 10.0 to 100.0 μg/kg. Generally it is sought to obtain a serum concentration of the relaxin approximating or greater than normal circulating levels of relaxin in pregnancy, i.e., 1.0 ng/ml, such as 1.0 to 20 ng/ml, preferably 1.0 to 20 ng/ml.

More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The agents may be systemic after administration or may be localized by the use of an implant that acts to retain the active dose at the site of implantation.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the targeted site, so that the local concentration of active agent is increased relative to the rest of the body.

The term “unit dosage form,” as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 μg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

Relaxin Analog Nucleic Acids

The invention includes novel nucleic acids encoding the analog polypeptides of the invention; and fragments and derivatives thereof. Nucleic acids of the invention are synthetically produced to encode the amino acid substitutions provided by the invention, and may utilize any appropriate combination of codons, as known in the art. For example, the codon usage may be tailored to provide efficiency in a host organism for recombinant production of the protein.

The subject nucleic acids can be DNA or RNA, as well as fragments thereof, particularly fragments that encode the biologically active polypeptide and/or are useful in the methods disclosed herein.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least about 18, about 50, about 100, to about 500 contiguous nt selected from the coding sequence. For the most part, fragments will be of at least 18 nt, usually at least 25 nt, and up to at least about 50 contiguous nt in length or more.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically “recombinant,” e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Regulation of Receptor Signaling by Relaxin A Chain Motifs

Derivation of Pan-Specific and LGR7-Specific Human Relaxin Analogs

Relaxin peptides are important hormones for the regulation of reproductive tissue remodeling and the renal cardiovascular system during pregnancy. Recent studies demonstrated that two of the seven human relaxin family peptides, relaxin H2 (RLN2) and INSL3, signal exclusively through leucine-rich repeat-containing G protein-coupled receptors, LGR7 and LGR8. Although it was well characterized that an RXXXRXXI motif at the RLN2 B chain confers receptor activation activity, it was previously not clear what roles RLN2 A chain plays in receptor interaction.

Analyses of relaxin family genes on syntenic regions of model tetrapods showed that the A chain of RLN2 orthologs exhibited a greater sequence divergence as compared with the receptor binding domain-containing B chain, foreshadowing a potential role in receptor interactions; hence, defining receptor selectivity in this fast evolving peptide hormone.

To test the hypothesis that select residues in the human RLN2 A chain play key roles in receptor interaction, we studied mutant peptides with residue substitution(s) in the A chain. It is shown herein that alanine substitution at the A16 and A17 positions enhances LGR8-activation activity of RLN2, whereas mutation at the A22-23 region (RLN2A22-23) ablates LGR8, but not LGR7, activation activity. In addition, we demonstrated that the functional characteristics of the RLN2A22-23 mutant are mainly attributed to modifications at the PheA23 position. Taken together, our studies indicated that ThrA16, LysA17, and PheA23 constitute part of the receptorbinding interface of human RLN2, and that modification of these residues has led to the generation of novel human RLN2 analogs that would allow selective activation of human LGR7, but not LGR8, in vivo.

Earlier studies showed that the replacement of 2 arginines and 1 isoleucine residue in the B chain of human RLN2 reduced the affinity by a 1000-fold, suggesting these three residues are critical for receptor interaction. X-ray crystallographic analysis indicates that these three residues are concentrated and form a binding surface for interaction with acidic residues in relaxin receptors. In addition, we have recently showed that a histidine residue in the B chain of INSL3 determines the receptor specificity of this peptide. Unlike the better characterized B chain, studies of porcine relaxin and human INSL3 variants with substitutions at the N terminus of the chain A indicated that no single amino acid in that region is functionally important.

Based on the observation that relaxin peptides from mammals exhibit distinct receptor selectivity and that relaxin homologs underwent positive selection in mammals, we hypothesized that structural motifs tolerant of divergence in RLN2 (e.g. the C terminus of A chain) could harbor microdomains important for the regulation of receptor selectivity; hence, the receptor activation. Consistent with our hypothesis, studies of recombinant RLN2 peptides with point mutation(s) show that ThrA16, LysA17, and PheA23 residues in the RLN2 A chain play critical roles in interacting with LGR7 and LGR8. In addition, these analyses have led to the generation of novel human RLN2 analogs that exhibit a greater preference for LGR7 as compared with the wild type peptide, as well as an analog that exhibits an enhanced bioactivity upon LGR8 activation.

Experimental Procedures

Syntenic Mapping and Identification of Ortliologous Relaxin Genes in Tetrapods. We analyzed the genomic DNAof human (*Homo sapiens*), chimpanzee (*Pan troglodytes*), the Rhesus monkey (*Macaca mulatta*), rat (*Rattus norvegicus*), mouse (*Mus musculus*), rabbit (*Oryctolagus cuniculus*), dog (*Canis familiaris*), cow (*Bos taurus)*, pig (*Sus scrofa*), nine-banded armadillo (*Dasypus novemcinctus*), elephant (*Loxodonta africana*), Madagascar hedgehog (*Echinops telfairi*), gray shorttailed opossum (*Monodelphis domestica*), platypus (*Ornithorhynchus anatinus*), chicken (*Gallus gallus*), and the clawed frog (*Xenopus tropicalis*), and identified homologs of human relaxin family genes including RLN1, RLN2, RLN3, INSL3, INSL4, INSL5, and INSL6.

The identity of relaxin family genes from different species was determined by syntenic mapping and a series of reciprocal pairwise sequence comparisons using the BLAST server. Chromosome fragments containing relaxin family genes syntenic to the RLN1/RLN2/INSL4/INSL6 locus on the human chromosome 9 from different tetrapod species were obtained from NCBI and Ensemble BioMart data bases based on syntenic mapping. The human-other mammal syntenic maps were downloaded from the Ensemble BioMart data mining tool. The exact locations for relaxin family genes in the syntenic chromosome regions were also verified by BLAT searches using the UCSC Genome Bioinformatics webserver.

Subcloning of Wild Type Human Relaxin Family Genes and Variants. Full-length cDNA for human RLN2, INSL3, and RLN3 were subcloned from a human testis and an ovary Marathon-ready cDNA library (Clontech, Mountain View, Calif.). To allow efficient secretion of recombinant peptides into the conditioned media by transfected cells, cDNAs encoding the proprotein region were appended with a signal peptide for secretion sequence from the prolactin precursor at the N terminus, and subcloned into the mammalian expression vector, pcDNA3.1 Zeo. Expression constructs for mutants with point mutation(s) and/or a truncated C domain were generated using overlapping PCR with specific primers in three steps. In the first PCR, forward and reverse primers were used to amplify acDNA stretch encoding the signal peptide and the downstream site of the introduced mutation. In the second PCR, a set of primers were used to amplify the cDNA encoding the mutation point as well as the remaining C-terminal region of propeptide. Products from the first and the second reactions were designed to share a 20-30-bp overlap in the region of the introduced mutation. After purification, the mixed templates from the first and second PCRs were amplified with primers of the 5'- and 3'-ends of the propeptide coding region. The full-length mutant cDNAs were gel purified and ligated into the pcDNA3.1 Zeo vector. The *Escherichia coli* strain, Top10, was electroporated for transformation, and the integrity of the construct was confirmed by automated dye-terminator cycle DNA sequencing.

Expression of Relaxin Family Peptides and Variants. For efficient detection and purification of recombinant peptides, all expression constructs were tagged with a Myc epitope at the N terminus and a 6-histidine ($His_6$) tag at the C terminus of the B chain. To allow efficient cleavage of the prepropeptide during post-translational modifications and the secretion of mature peptides, HEK293T cells were routinely cotransfected with the select expression construct and a one-tenth aliquot of a convertase expression vector. Cells were cultured in Dulbecco's modified Eagle's medium/F-12 media supplemented with 10% fetal bovine serum, 100 IU/ml penicillin, and 100 μg/ml streptomycin in a water-saturated atmosphere containing 5% $CO_2$ at 37° C. Transfection was performed using the calcium-phosphate precipitation method. Four days after transfection, conditioned media were collected, centrifuged, and filtered to remove cell debris. Recombinant peptides were then purified using nickel affinity chromatography.

Nickel Affinity Chromatography. After cleared of cell debris, the conditioned medium was incubated with nickel-conjugated chelating Sepharose Fast flow resin (Amersham Biosciences) overnight at 4° C. with stirring. The resins bound with tagged peptides were washed with 10 column volumes of washing buffer (Tris-buffered saline (TBS), pH 7.5) containing 20 mM imidazole, followed by 20 column volumes of the washing buffer containing 40 mM imidazole. The bound peptides were eluted and fractionated with TBS containing 200 mM imidazole. Fractions with immunoreactive peptides were combined and concentrated with Amicon Ultra columns (Millipore, Billerica, Mass.; Mr cutoff, 5,000) after washing with 20 column volumes of phosphate-buffered saline. The integrity and purity of the peptides were verified by Western blotting analysis using a monoclonal anti-Myc or an anti-relaxin B chain polyclonal antibody (Calbiochem, San Diego, Calif.) as well as Coomassie Blue staining. Purified peptides were quantified based on Western blotting analysis or a histidine peptide enzyme-linked immunosorbent assay. To ensure the fidelity of mutant peptides, for each construct at least two different batches of peptides from one-half liter of conditioned medium were generated and characterized independently.

SDS-PAGE and Western Blotting Analysis. Cell extracts, conditioned media, and affinity column-purified peptides were electrophoresed using 18% SDS-PAGE before being electrotransfered to polyvinylidine difluoride membranes (Hybond-P, Amersham Biosciences) in a Trans-Blot SD semi-dry transfer cell (Bio-Rad Laboratories). Samples were mixed with a loading buffer under nonreducing or reducing conditions (100 mM dithiothreitol and 5% β2-mercaptoethanol) before SDS-PAGE. Blots were then washed and blocked with 5% skim milk before immunoblotting using a primary antibody and a horseradish peroxidase-conjugated secondary IgG (1:5,000 final dilution in 3% skim milk). Signals were detected following immunofluorescent imaging using the ECL system (Amersham Biosciences).

Histidine Peptide Enzyme-linked Immunosorbent Assay. To quantify purified RLN2 peptides with different mutations, serial dilutions of peptides were bound to a His tag antibody plate (Novagen, Madison, Wis.) in 1× TBS with 3% bovine serum albumin. After a 3-h incubation, the plates were washed four times with 1× TBS containing 0.1% Tween 20, followed by incubation with a rabbit anti-relaxin antibody (1:2500 in TBS with 3% bovine serum albumin). After washing and incubating with a secondary horseradish peroxidase-conjugated goat antirabbit antibody (Amersham Biosciences), the signals were detected using TMB luciferase substrate (Calbiochem) with a luminometer (Bio-Rad).

Receptor-activation Analysis. The bioactivity of relaxin family peptides was determined based on the stimulation of adenylate cyclase activity in HEK293T cells stably expressing recombinant LGR7 or LGR8. Stable LGR7- or LGR8-expressing cells were maintained in Dulbecco's modified Eagle's medium/F-12 media supplemented with 200 ng/ml Zeocin (Invitrogen). After seeding at a density of $2\times10^5$ cells per well in 500 μl of Dulbecco's modified Eagle's medium/F-12 medium containing 0.1% bovine serum albumin in 48-well plates, cells were preincubated at 37° C. for 30 min in the presence of 0.25 mM 3-isobutyl-1-methylxanthine before treatment with increasing concentrations of peptides (from 0 to 100 nM) in quadruplicate. Twelve hours after treatment, the culture was reacted with acetic anhydride/triethylamine, and total cAMP content in cell lysates was measured using a specific cAMP radioimmunoassay. A nontagged human RLN2 peptide was used as a standard to verify the bioactivity of tagged RLN2 peptides.

Receptor-binding Assay. To determine the binding characteristics of wild type and mutant peptides, HEK293T cells expressing LGR7 or LGR8 were grown to 90% confluence, collected by centrifugation at 3000×g for 2 min, and washed two times in 2 ml of ice-cold binding buffer. Cells were resuspended in ice-cold binding buffer, and aliquots of cell suspension were incubated with increasing doses of purified recombinant peptides in the presence of 0.025 pmol of $^{125}I$-labeled RLN2 tracer (Phoenix Pharmaceuticals, Burlingame, Calif.) at room temperature for 2 h. After washing three times in an ice-cold binding buffer, radioactivity bound to the cells was measured using a γ-counter (EG&G Wallace, Gaithersburg, Md.). Total binding was determined in the absence, and nonspecific binding in the presence, of 25 nmol of unlabeled RLN2. In regular assays, total binding was ~30,000 cpm, and nonspecific binding amounted to less than 20% of the total binding. Data points were collected in triplicate, and similar results were obtained in at least two independent assays.

Mass Spectrometry Analysis of Recombinant Peptides. To confirm that the recombinant relaxin family peptides were processed similar to that of the native peptides and assumed a native conformation, the mass of purified peptides was determined by matrix-assisted laser desorption/ionization (MALDI) mass spectrometry. MALDI mass spectrometry was performed by the Pan facility at the Stanford University School of Medicine. Mass spectra were acquired on a Voyager DE-RP Model (Applied Biosystems, Foster City, Calif.).

Comparative Structure Modeling. To detect potential alterations in the surface motifs of RLN2 as a result of mutagenesis, we generated three-dimensional models of mutant peptides based on the human RLN2 crystal structure (Protein Data Bank 6RLN) using the SWISS-MODEL server and refined by energy minimization. Molecular views were drawn with the Swiss-PdbViewer and Protein Explorer 2.4 programs.

Statistical Analyses. Receptor-activation and receptorbinding activity curves generated in nonlinear regression analyses (Prism; GraphPad Software, San Diego, Calif.) were evaluated relative to the samples without hormone treatment. In all cases data are reported as the mean±S.E. of assays in triplicate or quadruplicate. Statistically significant responses ($p<0.05$) were determined for each stimulated response to the average nonspecific response from control samples using analysis of variance and Student's t test.

Results

Identification of Relaxin Homologs Syntenic to Human RLN2 in Prototherian, Metatherian, and Eutherian Mammals. To better understand the functional motifs important for receptor interaction in human RLN2, we analyzed the sequence conservation of orthologous relaxin peptides from mammals including monotremes, marsupials, and placentals as well as nonmammalian tetrapods. Although earlier studies have identified putative relaxin orthologs from a number of vertebrates, whether some of those genes are orthologous to human RLN2 has not been fully clarified as a result of divergent evolution of this family of genes in mammals. Our recent comparative genome analyses showed that relaxin family genes evolved from three independent loci including, 1) INSL5 or relaxin family locusA (RFLA) corresponding to human chromosome 1p31; 2) RLN1/RLN2/INSL4/INSL6 or relaxin family locus B (RFLB) corresponding to human chromosome 9p24; and 3) RLN3/INSL3 or relaxin family locus C (RFLC) corresponding to human chromosome 19p13 in the most recent common ancestor of vertebrates. The chromosomal regions syntenic to the human RFLB (RLN1/RLN2/INSL4/INSL6) locus could be identified in all studied species. In all therian mammals, this locus is marked by invariant flanking genes including RFX3, GLIS3, SLC1A1, RCL1, JAK2, C9orf46, CD274, and GLDC in neighboring loci (FIG. 1). Likewise, the single relaxin homolog at the syntenic regions of monotreme platypus and. X. tropicalis is flanked by orthologous RCL1, SLC1A1, and C9orf46 genes. Similar to humans, the chimpanzee genome encodes one of each of the orthologus RLN1, RLN2, INSL4, and INSL6 genes that cluster within a 171-kb region in tandem. Unlike hominids that share a common ancestor 5-10 million years ago, the Rhesus monkey genome encodes only one of each of the RLN, INSL4, and INSL6. On the other hand, placental mammals including the dog, rat, and mouse each contain one RLN and one INSL6, whereas the cow contains only an INSL6 ortholog (FIG. 1). Unlike the placental mammals, opossum, platypus, chicken, and *X. tropicalis* each contain only a single relaxin family gene at the syntenic RFLB locus.

These data indicate that the four human relaxin family paralogs in this locus were likely derived from nonallelic homologous recombinations at three separate geological times during the evolution of eutherians. The most likely scenario is that RLN1 and RLN2 evolved before the emergence of hominids. In contrast, INSL4 evolved before the divergence of old world monkeys and apes ~15 million years ago, whereas the ancestral RLN and INSL6 genes evolved only after the emergence of eutherian mammals ~90 million years ago. Sequence comparison of RLN homologs found at the syntenic RFLB locus of 15 mammals and that of chickens and *X. tropicalis* showed that the relaxin A chain exhibits a greater sequence divergence as compared with the RXXXRXXI motif-containing B chain (FIG. 2).

Based on this observation and earlier studies showing that relaxin orthologs from rodents exhibit a more restricted preference upon the activation of LGR7 versus LGR8 as compared with human and pig relaxins, we reasoned that the diverging C terminus of A chain could contain structural motifs important for interacting with LGR7 and/or LGR8, hence, receptor selectivity.

Figure 3:
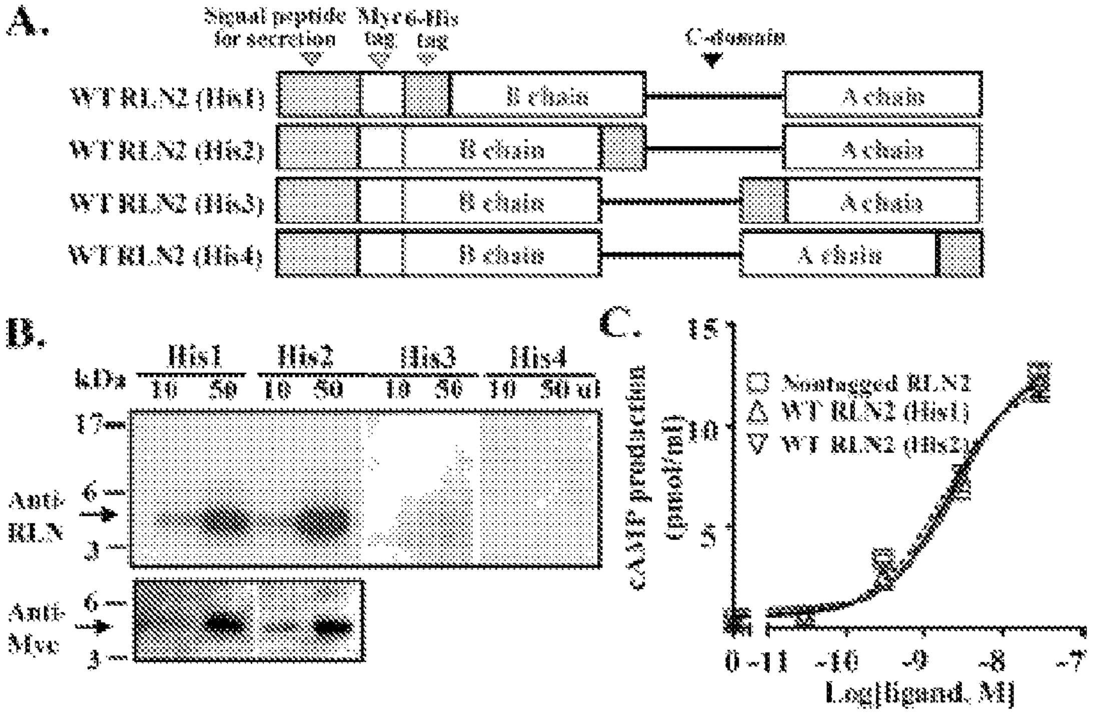
FIG. 3. Generation and characterization of tagged recombinant human RLN2 peptide. A, schematic design of recombinant RLN2 peptides with an N-terminal Myc tag and a $His_6$ tag at four different positions of the mature peptides (RLN2 His1-4). The mature B and A chains are indicated by a rectangle box, whereas the C domain is indicated by a line. Myc and $His_6$ epitopes are indicated by a light blue rectangle and a yellow rectangle, respectively. B, Western blotting analysis of tagged RLN2 peptides in conditioned media of transfected HEK293T cells using an anti-relaxin antibody (Calbiochem; upper panel) or an anti-Myc antibody (lower panel) under reducing conditions. The molecular weight standard is shown on the left. C, stimulation of cAMP production by RLN2 His1 and RLN2 His2 peptides in LGR7-expressing HEK293T cells.

Generation of Relaxin Family Peptides Using the Recombinant Approach. To test the hypothesis that human RLN2 A chain is important for receptor interaction, we generated and analyzed mutant RLN2 peptides with point mutations at various positions of the C terminus of A chain. Although relaxin peptides were mainly generated by synthetic chemistry approaches in earlier studies, recent studies showed that recombinant techniques provide an alternative approach to generate functional relaxin family peptides and different analogs. To allow routine generation of a variety of RLN2 mutants, we first analyzed the production of recombinant peptides with expression constructs in which the open reading frame of proRLN2 is tagged with a $His_6$ epitope at four different positions of the mature peptide in addition to an N-terminal Myc epitope (WT RLN2 His1, His2, His3, and His4; FIG. 3A).

Western blotting analysis shows that peptides tagged with a $His_6$ epitope at the N or C terminus of the B chain were efficiently secreted into the conditioned media, and the majority of secreted peptides exhibited a predicted 5-kDa molecular mass under reducing conditions (FIG. 3B). Similar to the nontagged wild type RLN2 peptide, RLN2 His1 and RLN2 His2 peptides stimulated adenylate cyclase activity in LGR7-expressing HEK293T cells with similar potencies (FIG. 3C and Table 1).

TABLE 1

Potencies of recombinant wild type (WT) and mutant RLN2 peptides on the activation of LGR7 and LGR8

| | $pEC_{50}$ | |
|---|---|---|
| Ligand | LGR7 | LGR8 |
| Nontagged RLN2 | 8.53 ± 0.10 | |
| WT RLN2 (His1) | 8.66 ± 0.09 | |
| WT RLN2 (His2) | 8.77 ± 0.10 | |
| RLN2 C-104 | 8.74 ± 0.05 | |
| RLN2 C-38 | 8.72 ± 0.10 | |
| RLN2 C-28 | 8.66 ± 0.07 | |
| RLN2 C-18 | 8.74 ± 0.09 | |
| RLN2 C-8 | 8.81 ± 0.10 | |
| WT RLN2 | 9.30 ± 0.04 | 7.41 ± 0.14 |
| WT RLN3 | 7.73 ± 0.07 | ND[a] |
| WT INSL3 | ND | 9.03 ± 0.05 |
| RLN2 $R^{B12}A$ | ND | ND |
| RLN2 $R^{B16}A$ | ND | ND |
| RLN2 $T^{A16}A$ | 9.75 ± 0.08 | 8.04 ± 0.06 |
| RLN2 $K^{A17}A$ | 9.18 ± 0.07 | 8.39 ± 0.06 |
| RLN2 $R^{A18}A$ | 9.67 ± 0.10 | 7.56 ± 0.04 |
| $RLN2^{A19-20}$ | 8.56 ± 0.07 | 8.41 ± 0.07 |
| $RLN2^{A22-23}$ | 8.87 ± 0.07 | ND |
| RLN2 $R^{A22}A$ | 10.03 ± 0.07 | 7.51 ± 0.09 |
| RLN2 $F^{A23}A$ | 9.45 ± 0.09 | ND |
| RLN2 $K^{A17}G$ | 9.04 ± 0.05 | 8.28 ± 0.05 |
| RLN2 $K^{A17}Q$ | 9.31 ± 0.11 | 7.77 ± 0.05 |
| RLN2 $K^{A17}D$ | 8.41 ± 0.06 | 8.36 ± 0.08 |

[a]ND, the $pEC_{50}$ values were not measurable.

Based on these observations, we tagged all expression constructs with an N terminus Myc epitope and a C terminus $His_6$ epitope flanking the mature B chain in subsequent studies. In addition, given that relaxin family peptides contain cryptic C domains of varying lengths and with multiple basic residues that could be subjected to alternative post-translational processing, we explored the possibility of generating relaxin peptides with a uniform C domain linker sequence to avoid differential processing of the secreted peptides. Studies of four expression constructs, in which the B and A chains of RLN2 were linked with a truncated C-domain of 8, 18, 28, or 38 amino acids (FIG. 4A, RLN2 C-8, RLN2 C-18, RLN2 C-28, and RLN2 C-38), revealed that the expression construct with as few as an 8-amino acid linker sequence allows efficient production of RLN2 in conditioned media (FIGS. 4B and 5B).

Figure 4:
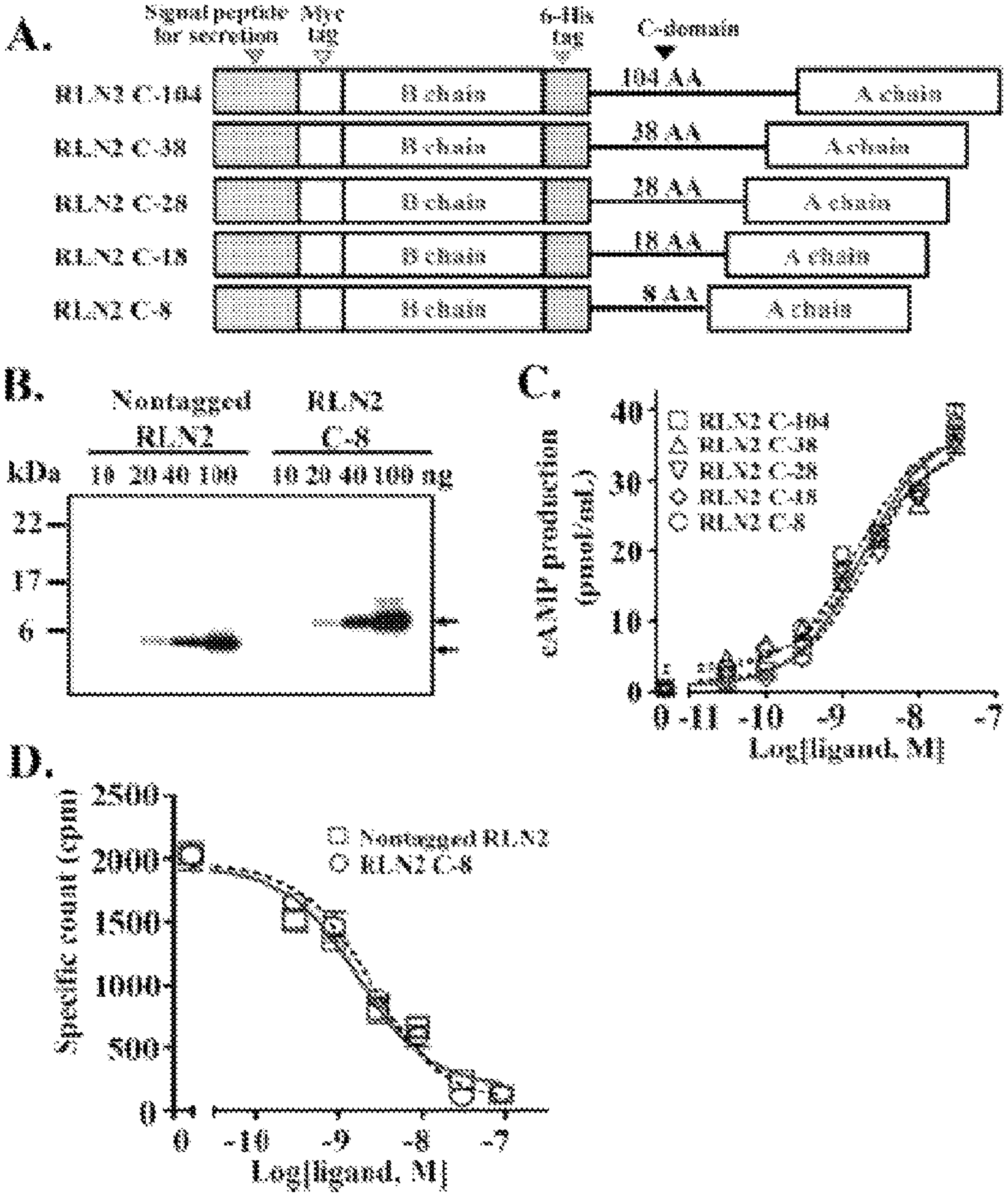
FIG. 4. Characterization of recombinant human RLN2 peptides generated using expression constructs with a truncated C domain linker sequence. A, schematic design of RLN2 expression constructs with a truncated C domain (RLN2 C-8 to C-38). The linker sequence was derived from the first 38-amino acids of the human RLN2 C domain and was flanked by a pair of dibasic cleavage sites for convertase cleavage. B, Western blotting analysis of a nontagged RLN2 peptide and the tagged RLN2 peptide generated using the expression construct with an 8-amino acid C domain sequence. Specific bands are detected using an anti-relaxin antibody, and are indicated by arrows. The molecular weight standard is shown on the left. C, stimulation of cAMP production by RLN2 peptides in LGR7-expressing HEK293T cells. Each data point represents the mean±S.E. of quadruplicate samples. D, competitive LGR7-binding analysis of the Myc- and $His_6$-tagged RLN2 C-8. Each data point represents the mean±S.E. of triplicate samples.
Figure 5:
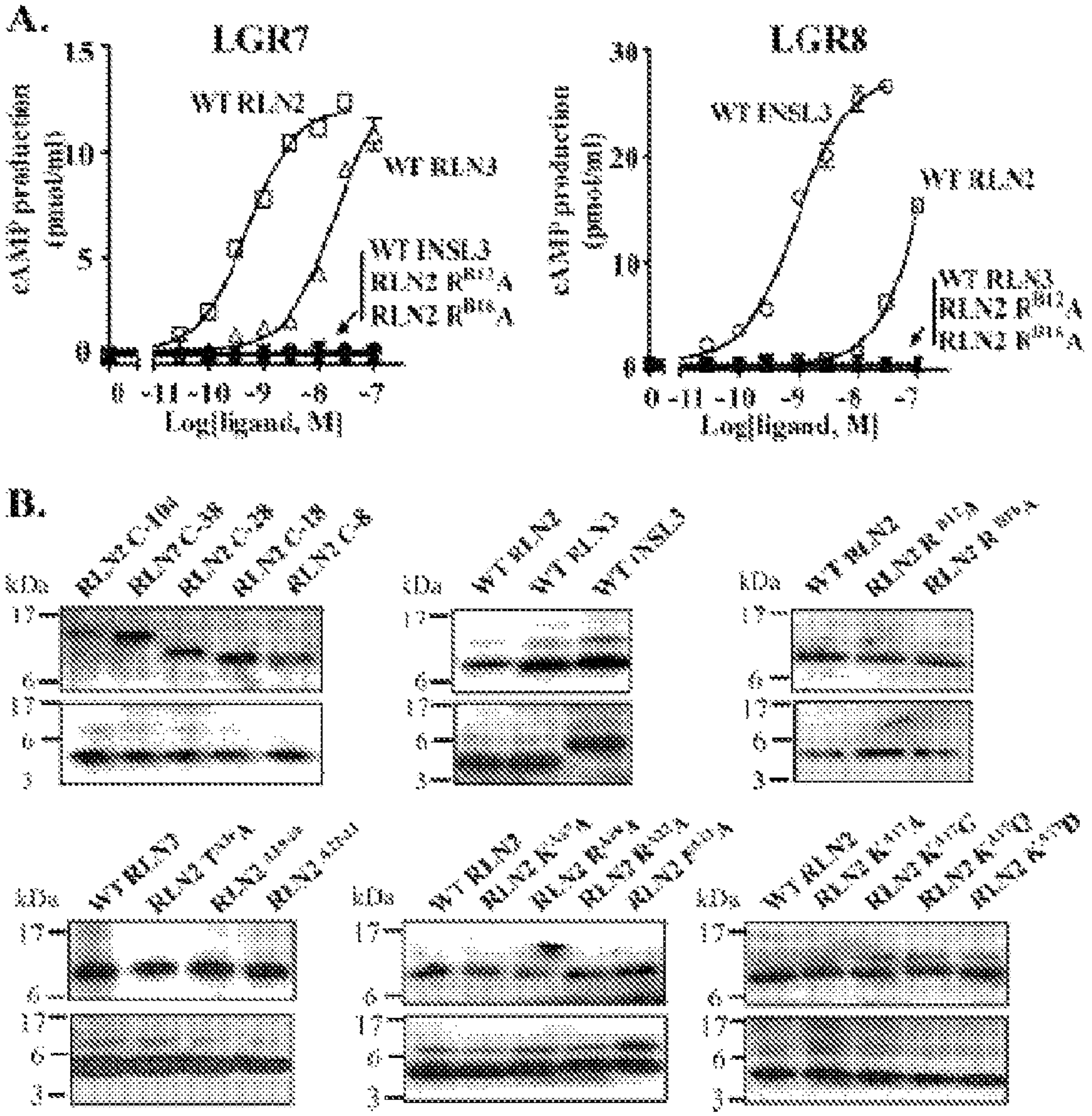
FIG. 5. Stimulation of cAMPproduction in LGR7- and LGR8-expressing cells by recombinant RLN2, RLN3, and INSL3. A, recombinant RLN3 and INSL3 selectively activated LGR7 and LGR8, respectively. In contrast, RLN2 activates both receptors at the nanomolar range. Unlike the wild type RLN2, substitution of $Arg^{B12}$ and $Arg^{B16}$ residues with alanine abolished the LGR7- and LGR8-activation activities of RLN2. Each data point represents the mean±S.E. of quadruplicate samples. B, Western blotting analysis of recombinant wild type and mutant relaxin peptides including, RLN2 C-104, C-38, C-28, C-18, C-8 (upper left), WT RLN2, WT RLN3, WT INSL3 (upper middle), WT RLN2, RLN2 $R^{B12}$A, RLN2 $R^{B16}$A (upper right), WTRLN2, RLN2 $T^{A16}$A, $RLN2^{A19-20}$, $RLN2^{A22-23}$ (lower left), WT RLN2, RLN2 $K^{A17}$A, RLN2 $R^{A18}$A, RLN2 $R^{A22}$A, RLN2 $F^{A23}$A (lower middle), WT RLN2, RLN2 $K^{A17}$A, RLN2 $K^{A17}$G, RLN2 $K^{A17}$Q, and RLN2 $K^{A17}$D (lower right). Affinity column purified peptides (100 ng/lane) were resolved by 18% SDS-PAGE under nonreducing (upper panel) and reducing (lower panel) conditions. The positions of molecular mass markers are indicated on the left.

Functional analyses showed that RLN2 generated using the RLN2 C-8, RLN2 C-18, RLN2 C-28, or RLN2 C-38 constructs all have an $EC_{50}$ upon LGR7 activation similar to that of RLN2 derived from the construct containing a 104- amino acid C domain sequence (FIG. 4C and Table 1). Similarly, receptor-binding analysis showed that the Myc epitope-tagged RLN2, derived from the RLN2 C-8 construct, competed for labeled nontagged RLN2 binding to LGR7 with a high affinity (FIG. 4D and Table 2). Subsequently, all our mutant expression constructs were engineered with an 8-amino acid miniature linker sequence between the B and A chains. Using the same approach, we also generated recombinant INSL3 and RLN3. Mass spectrometry analysis of purified peptides confirmed that these recombinant peptides are processed as heterodimeric peptides after post-translational cleavage of the C domain sequences (Table 3).

Importantly, functional analysis showed that recombinant peptides exhibit receptor activation characteristics similar to that of purified or chemically synthesized peptides. Unlike RLN3 and INSL3, which selectively activated LGR7 and LGR8, respectively, RLN2 activates both receptors at the nanomolar range (FIG. 5A). Furthermore, we show that alanine substitution at either of the charged residues of the RXXXRXXI motif (ArgB12 and ArgB16) ablated both the LGR7 and the LGR8 activation activity of RLN2 (FIG. 5A).

Figure 6:
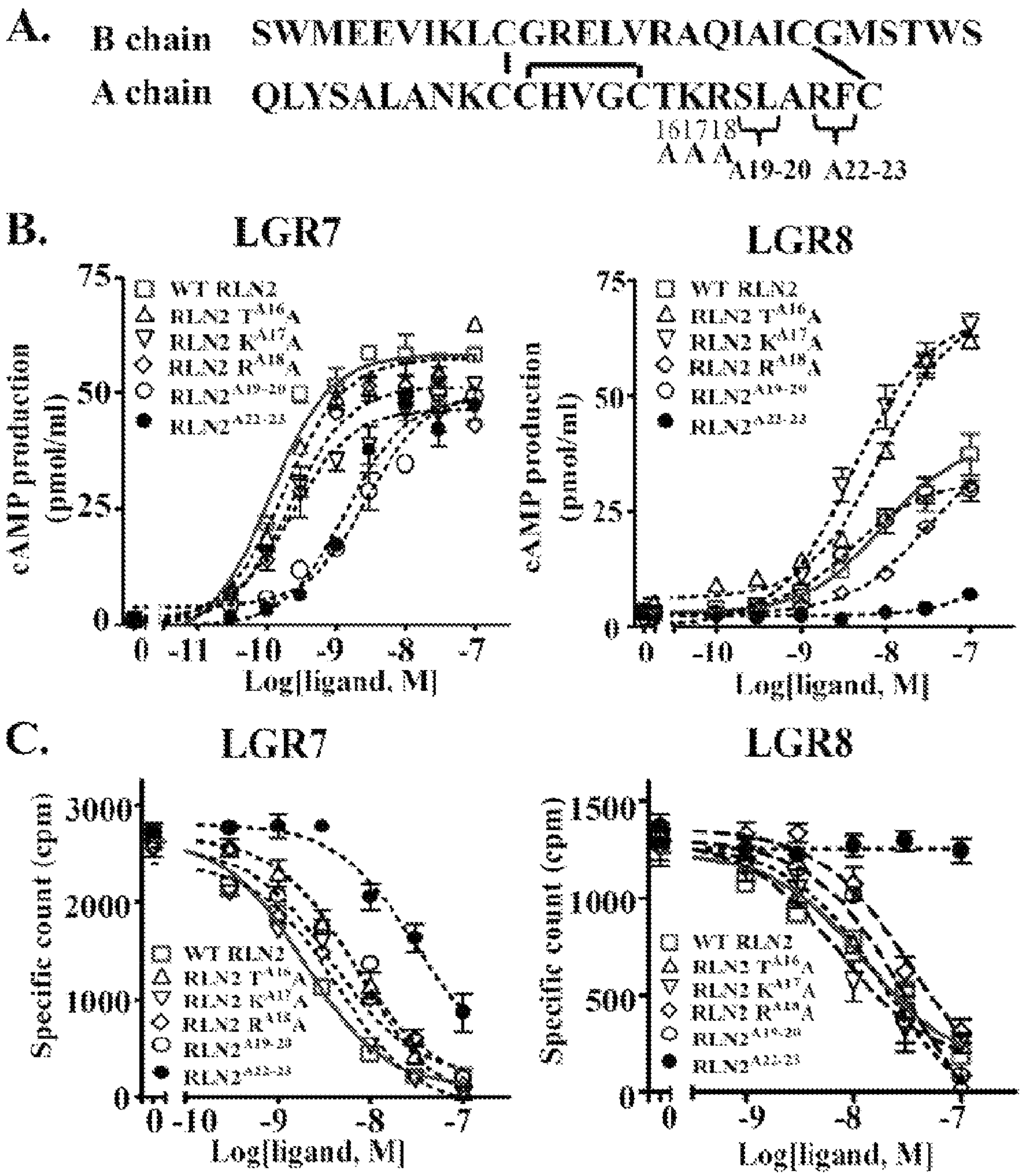
FIG. 6. Alanine substitution in the C terminus of A chain alters the receptor-activation activity of RLN2. A, schematic representation of RLN2 mutants with alanine substitution at five different positions of the A chain (RLN2 $T^{A16}$A, RLN2 $K^{A17}$A, RLN2 $R^{A18}$A, $RLN2^{A19-20}$, and $RLN2^{A22-23}$) shown in SEQ ID NO:25-26. B, stimulation of cAMP production in LGR7- and LGR8-expressing cells by the wild type and mutant RLN2 peptides. Unlike the wild type peptide, RLN2 $T^{A16}$A and RLN2 $K^{A17}$A mutants exhibited a significantly enhanced LGR8-activation activity. C, competitive LGR7- and LGR8-binding assays of wild type and mutant RLN2 peptides. Each data point in the receptoractivation and receptor-binding assays represents the mean ±S.E. of quadruplicate and triplicate samples, respectively.

A16-17 and A22-23 Regions in the RLN2 A Chain Play Critical Roles in Receptor Interaction. To investigate the role of residues at the C terminus of A chain in receptor interaction, we generated five mutants with alanine substitution at five different positions (FIG. 6A, RLN2 TA16A, RLN2 KA17A, RLN2 RA18A, RLN2A19-20, and RLN2A22-23). Western blotting analysis showed that all five mutants were processed to the mature form (FIG. 5B). Whereas RLN2 TA16A, RLN2 KA17A, and RLN2 RA18A mutants exhibited an $EC_{50}$ on LGR7 activation similar to that of the wild type peptides, RLN2A19-20 and RLN2A22-23 mutants exhibited decreased LGR7-activation activities (FIG. 6B, left panel, and Table 1). In addition, receptor-binding analyses shows that, except for RLN2A22-23, which exhibited a reduced affinity for LGR7, all other mutants competed for labeled RLN2 binding to LGR7 with affinities similar to that of wild type peptide (FIG. 6C, left panel, Table 2).

Although alanine substitution has minimal effects on maximum LGR7-activation activity of mutant peptides, mutation at the RLN2A16 and RLN2A17 positions leads to a 2-fold increase of the maximum LGR8-activation activity (FIG. 6B, right panel). In contrast, mutation of the RLN2A22-23 region almost abolished the LGR8-activation activity of RLN2. Consistent with analyses of receptor-activation activity, the RLN2 TA16A and RLN2 KA17A mutants exhibited an $IC_{50}$ value similar to that of wild type RLN2 for both LGR7 and LGR8, whereas the RLN2A22-23 mutant lost its LGR8-binding activity (FIG. 6C and Table 2).

Figure 7:
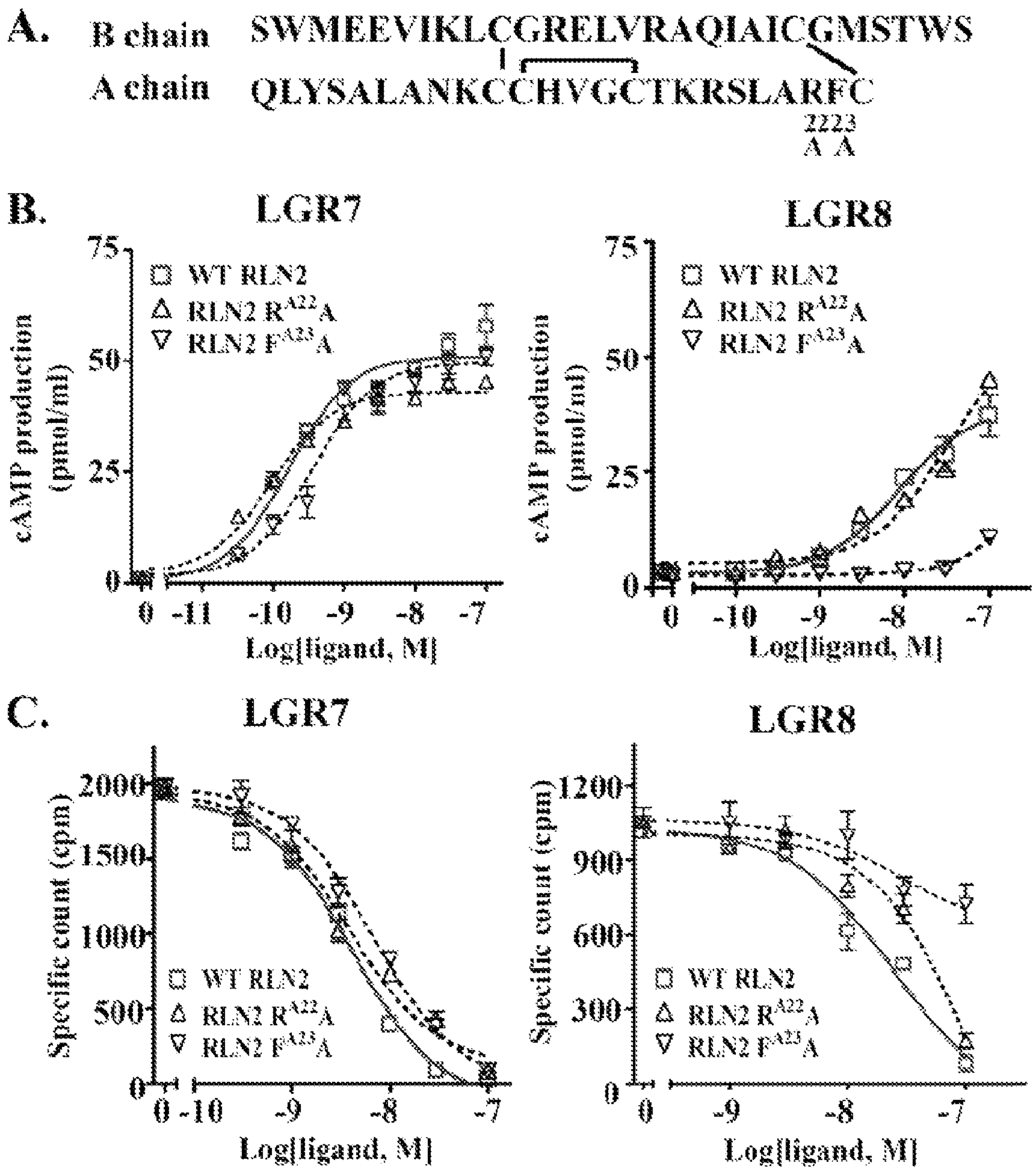
FIG. 7. Alanine substitution at the $Phe^{A23}$ position alters the receptor-interaction activities of RLN2. A, schematic representation of RLN2 mutants with alanine substitution at the $Arg^{A22}$ or $Phe^{A23}$ positions shown in SEQ ID NO:27-28. B, stimulation of cAMP production in LGR7- and LGR8-expressing cells by RLN2 $R^{A22}$A and RLN2 $F^{A23}$A mutants. $F^{A23}$A mutation ablated LGR8-activation activity. C, LGR7- and LGR8-binding activities of $R^{A22}$A and $F^{A23}$A mutant peptides. $F^{A23}$A mutation significantly reduced LGR8-binding activity, but without an effect on LGR7- binding activity. Each data point in the receptor-activation and receptor-binding assays represents the mean ±S.E. of quadruplicate and triplicate samples, respectively.

The Functional Characteristics of RLN2A22-23 Mutant Are Attributed to Mutation at the PheA23 Position. Given the findings that the A22-23 region plays important roles in receptor signaling, we then analyzed mutants with point mutation at ArgA22 and PheA23 positions (FIGS. 5B and 7A). Functional analysis showed that alanine substitution at the ArgA22 position has minimal effect on the LGR7- or LGR8-activation activity (FIG. 7B). In contrast, the RLN2 FA23A mutant lacks an LGR8-activation activity, but retains an LGR7-activation activity similar to that of wild type peptides. Receptor-binding assays showed that the RLN2 RA22A and RLN2 FA23A mutants bind to LGR7 with affinities similar to that of wild type peptides (FIG. 7C). In contrast, alanine substitution at the PheA23 position significantly reduced the affinity for LGR8 (FIG. 7C).

Figure 8:
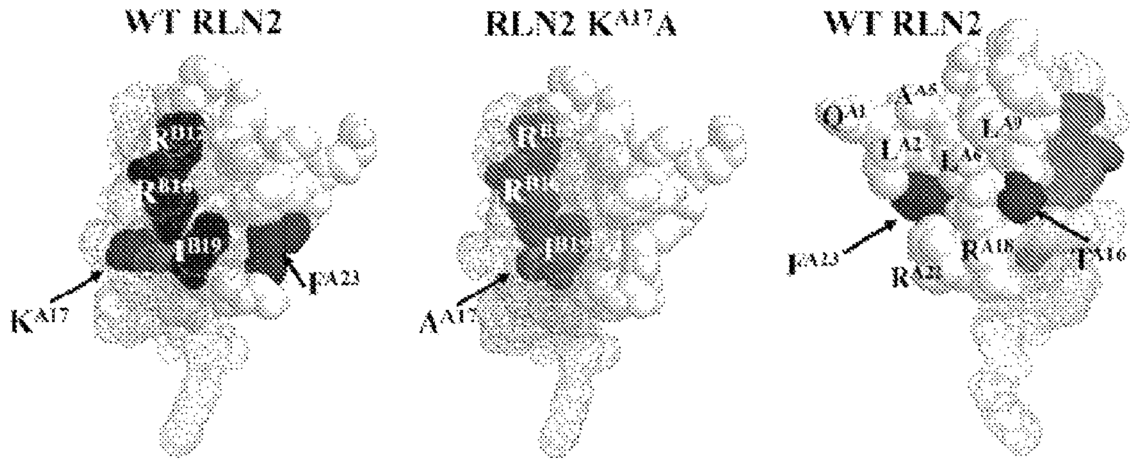
FIG. 8. Comparative structure modeling of mutant peptides based on the crystal structure of human RLN2. Three-dimensional structure of the wild type human RLN2 and the $K^{A17}$A mutant based on the RLN2 crystal structure (PDB 6RLN). The wild type RLN2 structure is shown on the left and right panels. The $K^{A17}$A mutant is shown on the middle panel. The A and B chains are indicted by white filled space and green dot space, respectively. The amino acids at A16, A17, and A23 positions are indicated by the brown filled space. The $Arg^{B12}$, $Arg^{B16}$, and $Ile^{B19}$ residues in the RXXXRXX1 motif of B chain are represented by the blue filled space.

ThrA16, LysA17, and PheA23 Residues Constitute Part of the Receptor-interacting Interface in Human RLN2. To gain a better understanding of the molecular basis for the regulation of receptor activation by ThrA16, LysA17, and PheA23, we generated simulated structure models of RLN2 mutants using the SWISS-MODEL server (FIG. 8). Comparative structure analyses showed that the LysA17 residue (brown filled space) is embedded between the interface of the A chain (white filled space) and the B chain (green dot space), and is the only A chain residue with its side chain exposed on the same surface with ArgB12, ArgB16, and IleB19 of the RXXXRXXI motif (FIG. 8, left panel). Alanine substitution in the RLN2 KA17A mutant eliminated the extended side chain of lysine that protrudes toward the B chain surface (FIG. 8, middle panel). Unlike the LysA17 residue, the ThrA16 and PheA23 residues are located opposite to the surface including LysA17 and the RXXXRXXI motif (FIG. 8, right panel). Judging by the orientation and the distance of these residues to the binding motif on the B chain, it likely interacts with a distinct ligand-binding interface of LGR7 and LGR8. The finding that the elimination of the extended side chain of lysine at the LysA17 position leads to an increased LGR8-activation activity was of particular interest considering its close proximity to the RXXXRXXI motif.

Figure 9:
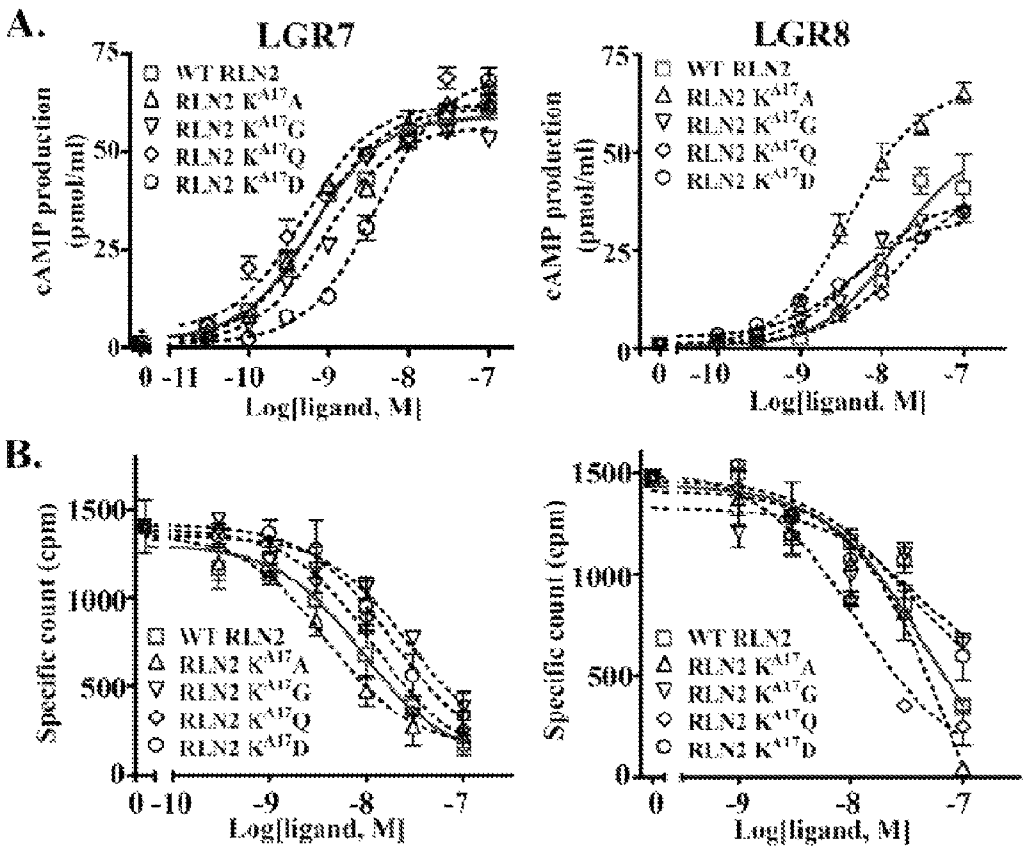
FIG. 9. Stimulation of cAMP production in LGR7- and LGR8-expressing cells by mutant peptides with residue substitution at the $Lys^{A17}$ position. A, stimulation of cAMP production in LGR7- and LGR8-expressing cells by $K^{A17}$A, $K^{A417}G$, $K^{417}D$, and $K^{A417}Q$ mutants. Unlike the $K^{A417}A$ peptide, mutants with an aspartic acid, glycine, or glutamine at the $Lys^{A17}$ position did not exhibit an enhanced LGR8-activation activity. Each data point represents the mean±S.E. of quadruplicate samples. B, LGR7- and LGR8-binding activities of $K^{A417}A$, $K^{A17}G$, $K^{A417}D$, and $K^{A17}Q$ mutants. Each data point represents the mean±S.E. of triplicate samples.

To further characterize the importance of the LysA17 position in receptor interaction, we analyzed the receptor activation activity of mutants with an aspartic acid, glutamine, or glycine at this position (FIG. 5B). Unlike the pan-specific RLN2 KA17A mutant, peptides with a glycine or glutamine at the LysA17 position exhibited normal LGR7- and LGR8-activation activity (FIGS. 9, A and B). Alternatively, substitution with an aspartic acid residue at the same position led to a reduced LGR7-activation activity (FIG. 9A). Receptor-binding assays showed that substitution with a glycine and aspartic acid at LysA17 reduced LGR7-binding activity by 3-fold (FIG. 9B). Conversely, glutamine substitution at LysA17 had a minimal effect on LGR7- or LGR8-binding activity.

Based on analyses of the receptor-activation and receptor binding activities, our study identified ThrA16, LysA17, and PheA23 of RLN2 as crucial residues in the interaction with LGR7 and LGR8, and suggested that these three residues act cooperatively with the well characterized RXXXRXXI motif in shaping the functional characteristics of human RLN2. These studies have also led to the generation of LGR7-specific human RLN2 analogs that are useful for selective activation of LGR7 signaling pathways in patients as well as a pan-specific analog with an enhanced LGR8-activation activity.

Relaxin family peptides are structurally similar to insulin and are first synthesized as a single chain prorelaxin, in which a C domain connecting the B and A chains is excised during the post-translational modification. Based on studies of insulin, which shares a similar three disulfide bridged two chain architecture, the C domain is thought to play a minimal role in the folding of a mature relaxin peptide. We show that, similar to insulin, a minimal linker sequence with only 8 amino acids is sufficient for the generation of mature RLN2, INSL3, and RLN3 peptides in transfected cells. These results suggest that the conformational propensities for a mature two-chain relaxin family peptide does not require a native C domain, and are consistent with the observation that the C domain sequence of these genes diverged greatly even among closely related species.

Unlike the C domain sequences, earlier studies of insulin and relaxin biosynthesis have shown that the A chain may function mainly as a scaffold in the assembly of a bioactive disulfide-bridged mature peptide. We show that RLN2 mutants with substitutions at various residues of the C terminus of the A chain were processed to mature forms, suggesting these residues play a minimal role in disulfide pairing and the folding of mature peptides.

Earlier structural-functional relationships of relaxin family peptides have been inferred from the degree of residue conservation among mammalian species and studies of native receptors. An invariant RXXXRXXI motif in the B chain was found to be essential for receptor binding, and replacement of arginines or isoleucine in this motif greatly reduced the binding activity. Although the molecular basis for the interaction between RXXXRXXI motif and the receptor is not clear, x-ray crystallographic structure analysis shows that the conserved arginines and isoleucine form a tight receptor-binding surface (34). Based on these observations, it was proposed that interactions between these charged residues and select acidic residues within the concave face of the ectodomain of LGR7 are critical to the receptor activation (58). In contrast, it was hypothesized that the isoleucine residue of the RLN2 B chain could interact with a cluster of tryptophan, isoleucine, and leucine residues close to the ligand-interacting acidic residues through hydrophobic interactions (38, 58). Similar to relaxin, a pair of arginines and a histidine in the INSL3 B chain were shown to be critical for receptor interaction (35, 37, 38, 50, 59). Interestingly, relaxin orthologs from placental mammals display varied preference for the two relaxin receptors even though all these orthologs contain the invariant RXXXRXXI motif (8, 40). Based on this observation, we hypothesized that: 1) the expansion of family genes at the syntenic RFLB locus in placental mammals has allowed the divergence in functional characteristics of relaxin peptides unrelated to the core structure of these peptides; and 2) analysis of residues at sites tolerant of substitutions could reveal molecular determinants that are critical to the optimal signaling in a select lineage. Indeed, in contrast to the general notion that the A chain has a minimal role in receptor interaction, we show that mutations at ThrA16, LysA17, and PheA23 positions significantly alter the receptor-binding and receptoractivation activities of RLN2. Whereas PheA23 is important for high affinity binding to LGR8, ThrA16 and LysA17 play a more critical role in restricting the interaction with LGR8. These findings are consistent with the hypothesis that residues at sites tolerant of substitutions in a rapidly expanding protein family could represent critical motifs important for lineage-specific adaptations. However, whether the difference in receptor selectivity of relaxin peptides from different mammals was attributed to residue difference at the C terminus of A chain remains to be investigated. Our study effectively expanded the known receptor-interacting interface of human RLN2, and indicated that ThrA16, LysA17, and PheA23 at the C terminus of the A chain, together with the RXXXRXXI motif, constitute a broad receptorbinding interface for optimal signal transmission. Of interest, structural modeling analyses show that LysA17 is the only residue with its side chain protruding onto the same surface with the RXXXRXXI motif and is in close proximity with ArgB12, ArgB16, and IleB19. Therefore, it is likely that LysA17 and the three receptor-binding residues in the RXXXRXXI motif form an extended binding interface to interact with the receptor. In contrast, ThrA16 and PheA23 are positioned on a surface opposite to that of the RXXXRXXI motif, suggesting that these residues could interact with a receptor interface distant from that for LysA17. It is important to note that depending on the amino acid introduced at the LysA17 position, the preference for LGR8 could be either enhanced or reduced. Whereas alanine substitution enhances LGR8-activation activity, corresponding substitution with a polar or a reverse charged residue reduces it. Therefore, the side chain at the LysA17 position could be conductive to conformational transformation and an alanine residue provides an induced fit for LGR8 activation. In contrast, a polar or a reversed charged residue at this position increases the hindrance for the adoption of an activation configuration for LGR8. In the last few years, human RLN2 has been the subject of various clinical studies aimed to treat etiology in reproduction and other systems (25-28). Based on the understanding that: 1) RLN2 activates LGR8 at the nanomolar concentration; and 2) LGR8 signaling is involved in the regulation of oocyte maturation, ovarian follicle development, and the positioning of the ovary (10, 22, 23, 60), it is conceivable that clinical application of the indiscriminative wild type human RLN2 could impose unwanted side effects on LGR8-medi-ated physiological processes in patients. The finding that RLN2A22-23, and FA23A mutants preferentially activate LGR7 thus provides novel agents to allow selective activation of LGR7-mediated physiological processes in patients. Although the related RLN3 activates only LGR7, but not LGR8, it also functions as a potent agonist for GPCR135 and GPCR142. In contrast, the RLN2 TA16A and RLN2 KA17A mutants, which exhibit high potencies on the activation of both LGR7 and LGR8, function as pan-specific agonists for these two receptors. These reagents could be useful in therapeutic applications that aim to activate both LGR7 and LGR8 in patients.

TABLE 2

Potencies of wild type (WT) and mutant RLN2 peptides in competition for RLN2 binding to LGR7 and LGR8

| Ligand | $pIC_{50}$ LGR7 | $pIC_{50}$ LGR8 |
|---|---|---|
| Nontagged RLN2 | 8.78 ± 0.12 | |
| RLN2 C-8 | 8.61 ± 0.09 | |
| WT RLN2 | 8.72 ± 0.06 | 7.90 ± 0.16 |
| RLN2 $T^{A16}$A | 8.40 ± 0.06 | 7.74 ± 0.07 |
| RLN2 $K^{A17}$A | 8.36 ± 0.08 | 8.14 ± 0.18 |
| RLN2 $R^{A18}$A | 8.42 ± 0.08 | 7.46 ± 0.17 |
| $RLN2^{A19-20}$ | 8.21 ± 0.10 | 7.51 ± 0.12 |
| $RLN2^{A22-23}$ | 7.50 ± 0.16 | ND[a] |
| RLN2 $R^{A22}$A | 8.42 ± 0.08 | 6.80 ± 0.32 |
| RLN2 $F^{A23}$A | 8.17 ± 0.06 | ND |
| RLN2 $K^{A17}$G | 7.57 ± 0.22 | 7.40 ± 0.41 |
| RLN2 $K^{A17}$Q | 7.93 ± 0.15 | 7.96 ± 0.11 |
| RLN2 $K^{A17}$D | 7.75 ± 0.25 | 7.53 ± 0.24 |

[a]ND, the $pIC_{50}$ values were not measurable.

TABLE 3

Mass spectrometry analysis of purified recombinant peptides

| Peptide | Molecular weight measured | Expected molecular weight |
|---|---|---|
| WT RLN2 | 8224 | 8225 |
| WT RLN3 | 7888 | 7888 |
| WT INSL3 | 8270 | 8272 |

Abbreviations used are: RLN1, relaxin H1; RLN2, relaxin H2; RLN3, relaxin 3; INSL3, insulin-like 3; GPCR, G protein-coupled receptor; LGR7, leucine-rich repeat-containing GPCR 7; LGR8, leucine-rich repeat-containing GPCR 8;MALDI, matrix-assisted laser desorption/ionization; TBS, Tris-buffered saline.

All publications and patent applications cited in this specification are herein incorporated by reference as if each individual publication or patent application were specifically and individually indicated to be incorporated by reference. The publications discussed herein are provided solely for their disclosure prior to the filing date of the present application.

Nothing herein is to be construed as an admission that the invention is not entitled to antedate such a disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A purified polypeptide analog of a mammalian relaxin 2 (RLN2) protein comprising an amino acid substitution to an amino acid other than the wild-type at residue 23 in the A chain, wherein the analog has increased selectivity for activation of the relaxin receptor LGR7 relative to the wild-type protein.

2. The polypeptide analog of claim 1, wherein the amino acid at residue 23 is selected from alanine, glycine, serine, threonine, isoleucine and leucine.

3. The polypeptide analog of claim 1, wherein the analog has enhanced biological activity relative to the wild-type protein.

4. The polypeptide analog according to claim 1, wherein the polypeptide analog is covalently linked to a RLN2 B chain.

5. The polypeptide analog of claim 4, wherein the RLN2 B chain has a wild-type amino acid sequence.

6. The polypeptide analog of claim 4, wherein the RLN2 B chain is a variant of the wild-type RLN2 B chain amino acid sequence.

7. The polypeptide analog according to claim 4, wherein the A chain and the B chain are covalently linked to a relaxin C chain.

8. The polypeptide analog of claim 7, wherein the C chain is a truncated C chain.

9. A pharmaceutical formulation comprising a polypeptide analog according to claim 1; and a pharmaceutically acceptable excipient.

10. A purified polypeptide analog of a mammalian relaxin 2 (RLN2) protein comprising an amino acid substitution at one or both of amino acid residues 16 and 17 to an amino acid other than the wild-type in the A chain, wherein the analog has increased activity for activation of the relaxin receptors LGR7 or LGR8 relative to the wild type protein.

11. The polypeptide analog of claim 10, wherein the polypeptide is a human RLN2 polypeptide comprising a substitution at residue 16 to an amino acid other than threonine.

12. The polypeptide analog of claim 10, wherein the polypeptide is a human RLN2 polypeptide comprising a substitution at residue 17 to an amino acid other than lysine.

13. The polypeptide analog of claim 11, wherein the amino acid at residue 16 or 17 is selected from alanine, glycine, isoleucine and leucine.

14. A purified polypeptide analog of a human relaxin 2 (RLN2) protein comprising:

an amino acid substitution at residue 23 in the A chain of a mammalian RLN2 protein to alanine, glycine, serine, threonine, isoleucine or leucine; and an amino acid substitution at one or both residues 16 and 17 in the A chain of said mammalian RLN2 protein to alanine, glycine, isoleucine or leucine;

wherein the analog has increased selectivity for the relaxin receptor LGR7 and enhanced biological activity relative to the wild-type protein.

15. The polypeptide analog according to claim 14, wherein the polypeptide analog is covalently linked to a RLN2 B chain.

16. The polypeptide analog of claim 15, wherein the RLN2 B chain has a wild-type amino acid sequence.

17. The polypeptide analog of claim 15, wherein the RLN2 B chain is a variant of the wild-type RLN2 B chain amino acid sequence.

18. The polypeptide analog according to claim 15, wherein the A chain and the B chain are covalently linked to a relaxin C chain.

19. The polypeptide analog of claim 18, wherein the C chain is a truncated C chain.

20. A pharmaceutical formulation comprising a polypeptide analog according to claim 14; and a pharmaceutically acceptable excipient.

* * * * *

SEQUENCE LISTING

```
<160> NUMBER OF SEQ ID NOS: 28

<210> SEQ ID NO 1
<211> LENGTH: 185
<212> TYPE: PRT
<213> ORGANISM: Homo sapiens
<220> FEATURE:
<223> OTHER INFORMATION: RLN2 polypeptide

<400> SEQUENCE: 1

Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Asn Met Met Ser Glu Phe Val Ala Asn Leu Pro Gln
                85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
    130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185


<210> SEQ ID NO 2
<211> LENGTH: 28
<212> TYPE: PRT
<213> ORGANISM: Homo sapiens
<220> FEATURE:
<223> OTHER INFORMATION: wt human mature B chain

<400> SEQUENCE: 2

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser
            20                  25


<210> SEQ ID NO 3
<211> LENGTH: 24
<212> TYPE: PRT
<213> ORGANISM: Homo sapiens
<220> FEATURE:
<223> OTHER INFORMATION: wt human RLN2 A chain
```

<400> SEQUENCE: 3

Gln Leu Tyr Ser Ala Leu Ala Asn Lys Cys Cys His Val Gly Cys Thr
 1               5                   10                  15

Lys Arg Ser Leu Ala Arg Phe Cys
            20

<210> SEQ ID NO 4
<211> LENGTH: 108
<212> TYPE: PRT
<213> ORGANISM: Homo sapiens
<220> FEATURE:
<223> OTHER INFORMATION: wt C chain of human RLN2

<400> SEQUENCE: 4

Lys Arg Ser Leu Ser Gln Glu Asp Ala Pro Gln Thr Pro Arg Pro Val
 1               5                   10                  15

Ala Glu Ile Val Pro Ser Phe Ile Asn Lys Asp Thr Glu Thr Ile Asn
            20                  25                  30

Met Met Ser Glu Phe Val Ala Asn Leu Pro Gln Glu Leu Lys Leu Thr
        35                  40                  45

Leu Ser Glu Met Gln Pro Ala Leu Pro Gln Leu Gln Gln His Val Pro
    50                  55                  60

Val Leu Lys Asp Ser Ser Leu Leu Phe Glu Glu Phe Lys Lys Leu Ile
65                  70                  75                  80

Arg Asn Arg Gln Ser Glu Ala Ala Asp Ser Ser Pro Ser Glu Leu Lys
                85                  90                  95

Tyr Leu Gly Leu Asp Thr His Ser Arg Lys Lys Arg
            100                 105

<210> SEQ ID NO 5
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 23
<223> OTHER INFORMATION: Xaa = Any amino acid except phenylalanine

<400> SEQUENCE: 5

Gln Leu Tyr Ser Ala Leu Ala Asn Lys Cys Cys His Val Gly Cys Thr
 1               5                   10                  15

Lys Arg Ser Leu Ala Arg Xaa Cys
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 16, 17
<223> OTHER INFORMATION: Xaa = Any amino acid except threonine and
      lysine

<400> SEQUENCE: 6

Gln Leu Tyr Ser Ala Leu Ala Asn Lys Cys Cys His Val Gly Cys Xaa
 1               5                   10                  15

Xaa Arg Ser Leu Ala Arg Phe Cys
            20

<210> SEQ ID NO 7
<211> LENGTH: 51
<212> TYPE: PRT
<213> ORGANISM: H. sapiens

<400> SEQUENCE: 7

```
Lys Trp Lys Asp Asp Val Ile Lys Leu Cys Gly Arg Glu Leu Val Arg
 1               5                  10                  15

Ala Gln Ile Ala Ile Cys Gly Met Ser Thr Trp Arg Pro Tyr Val Ala
            20                  25                  30

Leu Phe Glu Lys Cys Cys Leu Ile Gly Cys Thr Lys Arg Ser Leu Ala
        35                  40                  45

Lys Tyr Cys
    50
```

<210> SEQ ID NO 8
<211> LENGTH: 51
<212> TYPE: PRT
<213> ORGANISM: H. sapiens

<400> SEQUENCE: 8

```
Ser Trp Met Glu Glu Val Ile Lys Leu Cys Gly Arg Glu Leu Val Arg
 1               5                  10                  15

Ala Gln Ile Ala Ile Cys Gly Met Ser Thr Trp Gln Leu Tyr Ser Ala
            20                  25                  30

Leu Ala Asn Lys Cys Cys His Val Gly Cys Thr Lys Arg Ser Leu Ala
        35                  40                  45

Arg Phe Cys
    50
```

<210> SEQ ID NO 9
<211> LENGTH: 51
<212> TYPE: PRT
<213> ORGANISM: M. mulatta

<400> SEQUENCE: 9

```
Lys Trp Met Asp Asp Val Ile Lys Ala Cys Gly Arg Glu Leu Val Arg
 1               5                  10                  15

Ala Gln Ile Ala Ile Cys Gly Lys Ser Thr Leu Gln Leu Tyr Met Thr
            20                  25                  30

Leu Ser Asn Lys Cys Cys His Ile Gly Cys Thr Lys Lys Ser Leu Ala
        35                  40                  45

Lys Phe Cys
    50
```

<210> SEQ ID NO 10
<211> LENGTH: 51
<212> TYPE: PRT
<213> ORGANISM: G. alleni

<400> SEQUENCE: 10

```
Lys Trp Met Asp Asp Val Ile Lys Ala Cys Gly Arg Glu Leu Val Arg
 1               5                  10                  15

Ala Gln Ile Ala Ile Cys Gly Lys Ser Thr Leu Gln Leu Tyr Met Thr
            20                  25                  30

Leu Ser Asn Lys Cys Cys His Ile Gly Cys Thr Lys Lys Ser Leu Ala
        35                  40                  45

Lys Phe Cys
    50
```

<210> SEQ ID NO 11
<211> LENGTH: 52
<212> TYPE: PRT
<213> ORGANISM: E. caballus

<400> SEQUENCE: 11

```
Glu Asn Leu Asn Gln Ile Ile Phe Ala Cys Gly Arg Arg Leu Ile Arg
 1               5                  10                  15

Ile Trp Val Glu Val Cys Gly Ser Thr Gly Phe Glu Arg Tyr Met Ser
            20                  25                  30

Pro Leu Gln Lys Cys Cys Arg Ile Gly Cys Thr Lys Arg Ser Leu Ala
        35                  40                  45

Arg Phe Phe Cys
    50
```

<210> SEQ ID NO 12
<211> LENGTH: 51
<212> TYPE: PRT
<213> ORGANISM: Elephas maximus

<400> SEQUENCE: 12

```
Gln Lys Pro Asp Asp Val Ile Lys Ala Cys Gly Arg Glu Leu Ala Arg
 1               5                  10                  15

Leu Arg Ile Glu Ile Cys Gly Ser Leu Ser Trp Lys Arg Met Ile Gln
            20                  25                  30

Leu Ser His Lys Cys Cys Tyr Trp Gly Cys Thr Arg Lys Glu Leu Ala
        35                  40                  45

Arg Gln Cys
    50
```

<210> SEQ ID NO 13
<211> LENGTH: 51
<212> TYPE: PRT
<213> ORGANISM: Camelus dromedarius

<400> SEQUENCE: 13

```
Glu Arg Ser Asn Asp Phe Val Lys Ala Cys Gly Arg Glu Leu Val Arg
 1               5                  10                  15

Leu Trp Ile Glu Ile Cys Gly Ser Val Ser Trp Gln Leu Gln Met Thr
            20                  25                  30

Leu Gly Glu Arg Cys Cys Gln Lys Gly Cys Ser Arg Lys Glu Met Ala
        35                  40                  45

Thr Ala Cys
    50
```

<210> SEQ ID NO 14
<211> LENGTH: 50
<212> TYPE: PRT
<213> ORGANISM: Sus scrofa

<400> SEQUENCE: 14

```
Gln Ser Thr Asn Asp Phe Ile Lys Ala Cys Gly Arg Glu Leu Val Arg
 1               5                  10                  15

Leu Trp Val Glu Ile Cys Gly Ser Val Ser Trp Leu Phe Arg Met Thr
            20                  25                  30

Leu Ser Glu Lys Cys Cys Val Gly Cys Ile Arg Lys Asp Ile Ala Arg
        35                  40                  45

Leu Cys
    50
```

-continued

<210> SEQ ID NO 15
<211> LENGTH: 51
<212> TYPE: PRT
<213> ORGANISM: C. familiaris

<400> SEQUENCE: 15

```
Ala Thr Asp Asp Lys Lys Leu Lys Ala Cys Gly Arg Asp Tyr Val Arg
 1               5                  10                  15

Leu Gln Ile Glu Val Cys Gly Ser Ile Trp Trp Asp Asn Tyr Ile Lys
            20                  25                  30

Met Ser Asp Lys Cys Cys Asn Val Gly Cys Thr Arg Arg Glu Leu Ala
        35                  40                  45

Ser Arg Cys
    50
```

<210> SEQ ID NO 16
<211> LENGTH: 51
<212> TYPE: PRT
<213> ORGANISM: felis cattus

<400> SEQUENCE: 16

```
Ala Thr Asp Asp Lys Lys Leu Lys Ala Cys Gly Arg Asp Tyr Val Arg
 1               5                  10                  15

Leu Gln Ile Glu Val Cys Gly Ser Ile Trp Trp Asp Asn Tyr Ile Lys
            20                  25                  30

Met Ser Asp Lys Cys Cys Asn Val Gly Cys Thr Arg Arg Glu Leu Ala
        35                  40                  45

Ser Arg Cys
    50
```

<210> SEQ ID NO 17
<211> LENGTH: 51
<212> TYPE: PRT
<213> ORGANISM: Myotis lucifugus

<400> SEQUENCE: 17

```
Gly Gln Asp Thr Glu Ile Phe Thr Lys Cys Asn Leu Glu Leu Val Arg
 1               5                  10                  15

Phe Phe Ile Arg Val Cys Gly Thr His Ile Trp Glu Val Pro Tyr Arg
            20                  25                  30

Leu Ser Asp Lys Cys Cys Asn Val Gly Cys Thr Lys Lys Glu Val Ala
        35                  40                  45

Val Tyr Cys
    50
```

<210> SEQ ID NO 18
<211> LENGTH: 52
<212> TYPE: PRT
<213> ORGANISM: M. musculus

<400> SEQUENCE: 18

```
Glu Trp Met Asp Gly Phe Ile Arg Met Cys Gly Arg Glu Tyr Ala Arg
 1               5                  10                  15

Glu Leu Ile Lys Ile Cys Gly Ala Ser Val Gly Glu Ser Gly Gly Leu
            20                  25                  30

Met Ser Gln Gln Cys Cys His Val Gly Cys Ser Arg Arg Ser Ile Ala
        35                  40                  45

Lys Leu Tyr Cys
    50
```

<210> SEQ ID NO 19
<211> LENGTH: 52
<212> TYPE: PRT
<213> ORGANISM: R. norvegicus

<400> SEQUENCE: 19

```
Glu Trp Met Asp Gly Phe Ile Arg Met Cys Gly Arg Glu Tyr Ala Arg
 1               5                  10                  15

Glu Leu Ile Lys Ile Cys Gly Ala Ser Val Gly Glu Ser Gly Gly Leu
            20                  25                  30

Met Ser Gln Gln Cys Cys His Val Gly Cys Ser Arg Arg Ser Ile Ala
        35                  40                  45

Lys Leu Tyr Cys
    50
```

<210> SEQ ID NO 20
<211> LENGTH: 50
<212> TYPE: PRT
<213> ORGANISM: Cavia porcellus

<400> SEQUENCE: 20

```
Gly Phe Leu Asp Lys Val Ile Lys Val Cys Gly Arg Asp Leu Val Arg
 1               5                  10                  15

Ile Lys Ile Asp Ile Cys Gly Lys Ile Leu Leu Gln Leu Asp Met Thr
            20                  25                  30

Val Ser Glu Lys Cys Cys Gln Val Gly Cys Thr Arg Arg Phe Ile Ala
        35                  40                  45

Asn Ser
    50
```

<210> SEQ ID NO 21
<211> LENGTH: 51
<212> TYPE: PRT
<213> ORGANISM: M. domestica

<400> SEQUENCE: 21

```
Lys Phe Glu Asp Thr Pro Met Lys Leu Cys Gly Arg Glu Phe Ile Arg
 1               5                  10                  15

Ala Val Ile Phe Thr Cys Gly Gly Ser Arg Trp Asp Ser Ser Thr Gly
            20                  25                  30

Ile Ala Asp Tyr Cys Cys Gln Val Ser Cys Thr Lys Asn Asp Ile Ala
        35                  40                  45

Lys Leu Cys
    50
```

<210> SEQ ID NO 22
<211> LENGTH: 51
<212> TYPE: PRT
<213> ORGANISM: O. anatinus

<400> SEQUENCE: 22

```
Glu Thr Gly Pro Asp Lys Met Lys Leu Cys Gly Arg Glu Phe Ile Arg
 1               5                  10                  15

Thr Val Ile Phe Thr Cys Gly Gly Ser Arg Trp Lys Arg Asp Phe Ser
            20                  25                  30

Leu Gly Ser Tyr Cys Cys Thr Tyr Ser Cys Ser Lys Ala Asp Ile Ile
        35                  40                  45

Lys Val Cys
    50
```

<210> SEQ ID NO 23
<211> LENGTH: 53
<212> TYPE: PRT
<213> ORGANISM: G. gallus

<400> SEQUENCE: 23

```
Asp Gly Asp Gly Tyr Gly Val Lys Leu Cys Gly Arg Glu Phe Ile Arg
 1               5                  10                  15

Ala Val Ile Phe Thr Cys Gly Gly Ser Arg Trp Arg Glu Ser Leu Gly
            20                  25                  30

Leu Ala Gly Met Cys Cys Lys Trp Gly Cys Thr Lys Ala Glu Ile Ser
        35                  40                  45

Thr Ile Cys Arg Val
    50
```

<210> SEQ ID NO 24
<211> LENGTH: 51
<212> TYPE: PRT
<213> ORGANISM: X. tropicalus

<400> SEQUENCE: 24

```
Ala Ala Gly Glu Tyr Gly Val Lys Leu Cys Gly Arg Glu Phe Ile Arg
 1               5                  10                  15

Ala Val Ile Phe Thr Cys Gly Gly Ser Arg Trp Glu Met Asn Ile Gly
            20                  25                  30

Val Ala Gly Ile Cys Cys Lys Trp Gly Cys Thr Lys Ala Glu Ile Ser
        35                  40                  45

Thr Leu Cys
    50
```

<210> SEQ ID NO 25
<211> LENGTH: 28
<212> TYPE: PRT
<213> ORGANISM: H. sapiens

<400> SEQUENCE: 25

```
Ser Trp Met Glu Glu Val Ile Lys Leu Cys Gly Arg Glu Leu Val Arg
 1               5                  10                  15

Ala Gln Ile Ala Ile Cys Gly Met Ser Thr Trp Ser
            20                  25
```

<210> SEQ ID NO 26
<211> LENGTH: 24
<212> TYPE: PRT
<213> ORGANISM: H. sapiens

<400> SEQUENCE: 26

```
Gln Leu Tyr Ser Ala Leu Ala Asn Lys Cys Cys His Val Gly Cys Thr
 1               5                  10                  15

Lys Arg Ser Leu Ala Arg Phe Cys
            20
```

<210> SEQ ID NO 27
<211> LENGTH: 28
<212> TYPE: PRT
<213> ORGANISM: H. sapiens

<400> SEQUENCE: 27

```
Ser Trp Met Glu Glu Val Ile Lys Leu Cys Gly Arg Glu Leu Val Arg
 1               5                  10                  15
```

-continued

```
Ala Gln Ile Ala Ile Cys Gly Met Ser Thr Trp Ser
            20                  25


<210> SEQ ID NO 28
<211> LENGTH: 24
<212> TYPE: PRT
<213> ORGANISM: H. sapiens

<400> SEQUENCE: 28

Gln Leu Tyr Ser Ala Leu Ala Asn Lys Cys Cys His Val Gly Cys Thr
 1               5                  10                  15

Lys Arg Ser Leu Ala Arg Phe Cys
            20
```